(12) United States Patent
Hartwell

(10) Patent No.: US 12,029,549 B2
(45) Date of Patent: Jul. 9, 2024

(54) APPARATUS AND METHOD FOR WOUND VOLUME MEASUREMENT

(71) Applicant: Smith & Nephew PLC, Watford (GB)

(72) Inventor: Edward Yerbury Hartwell, Hull (GB)

(73) Assignee: Smith & Nephew PLC, Watford (GB)

( * ) Notice: Subject to any disclaimer, the term of this patent is extended or adjusted under 35 U.S.C. 154(b) by 387 days.

(21) Appl. No.: 17/381,037

(22) Filed: Jul. 20, 2021

(65) Prior Publication Data

US 2022/0008640 A1 Jan. 13, 2022

Related U.S. Application Data

(60) Continuation of application No. 15/994,818, filed on May 31, 2018, now abandoned, which is a (Continued)

(30) Foreign Application Priority Data

Dec. 6, 2007 (GB) ...................................... 0723855

(51) Int. Cl.
*A61B 5/107* (2006.01)
*A61B 5/00* (2006.01)
(Continued)

(52) U.S. Cl.
CPC ............ *A61B 5/107* (2013.01); *A61B 5/0055* (2013.01); *A61B 5/1073* (2013.01); *A61B 5/445* (2013.01);
(Continued)

(58) Field of Classification Search
CPC .......... A61M 5/00; A61M 3/00; A61M 25/00; A61M 35/00; A61M 1/00; A61M 5/178;
(Continued)

(56) References Cited

U.S. PATENT DOCUMENTS 3,572,340 A 3/1971 Lloyd et al.
3,787,882 A 1/1974 Fillmore et al.
(Continued)

FOREIGN PATENT DOCUMENTS

CN 101378795 A 3/2009
CN 101385887 A 3/2009
(Continued)

OTHER PUBLICATIONS

Annex to the Communication, re the Opposition of European Patent No. EP 2237724, dated Oct. 30, 2017, 15 pages.
(Continued)

*Primary Examiner* — Adam Marcetich
*Assistant Examiner* — Ted Yang
(74) *Attorney, Agent, or Firm* — Knobbe, Martens, Olson & Bear, LLP

(57) ABSTRACT

A method and apparatus for measuring a volume of a wound are described, the method comprising the steps of: applying a dressing over a wound, the volume of which is to be measured, the dressing including at least a sealing drape over the wound so as to create a sealed wound cavity; creating a vacuum in said wound cavity by vacuum pump means so as to produce a predetermined vacuum in the wound cavity; measuring a volume of air extracted from said wound cavity in producing said predetermined vacuum; and, calculating a volume of said wound.

18 Claims, 9 Drawing Sheets

Related U.S. Application Data continuation of application No. 14/946,468, filed on Nov. 19, 2015, now Pat. No. 9,987,402, which is a continuation of application No. 14/455,200, filed on Aug. 8, 2014, now Pat. No. 9,192,332, which is a division of application No. 12/746,492, filed as application No. PCT/GB2008/050917 on Oct. 7, 2008, now Pat. No. 8,814,841.

(51) Int. Cl.
*A61F 13/00* (2024.01)
*A61M 1/00* (2006.01)

(52) U.S. Cl.
CPC .......... *A61B 5/7278* (2013.01); *A61B 5/742* (2013.01); *A61F 13/00* (2013.01); *A61M 1/73* (2021.05); *A61B 5/6843* (2013.01); *A61M 1/982* (2021.05); *A61M 2205/15* (2013.01); *A61M 2205/18* (2013.01); *A61M 2205/3331* (2013.01); *A61M 2205/3344* (2013.01); *A61M 2205/50* (2013.01); *A61M 2230/00* (2013.01)

(58) Field of Classification Search
CPC .... A61M 1/73; A61M 1/982; A61M 2205/15; A61M 2205/18; A61M 2205/3331; A61M 2205/3344; A61M 2205/50; A61M 2230/00; A61M 1/90; A61M 1/96; A61F 7/00; A61F 13/00; A61B 5/107; A61B 5/0055; A61B 5/1073; A61B 5/445; A61B 5/7278; A61B 5/742; A61B 5/6843
See application file for complete search history.

(56) References Cited

U.S. PATENT DOCUMENTS

| | | |
|---|---|---|
| 3,972,328 A | 8/1976 | Chen |
| 4,015,912 A | 4/1977 | Kofink |
| 4,062,012 A | 12/1977 | Colbert et al. |
| 4,599,052 A | 7/1986 | Langen et al. |
| 4,643,641 A | 2/1987 | Clausen et al. |
| 4,710,165 A | 12/1987 | McNeil et al. |
| 4,969,880 A | 11/1990 | Zamierowski |
| 5,127,388 A | 7/1992 | Cicalese et al. |
| 5,173,033 A | 12/1992 | Adahan |
| 5,222,714 A | 6/1993 | Morinigo et al. |
| 5,238,732 A | 8/1993 | Krishnan |
| 5,291,822 A | 3/1994 | Alsobrooks et al. |
| 5,349,896 A | 9/1994 | Delaney, III et al. |
| 5,358,494 A | 10/1994 | Svedman |
| 5,360,445 A | 11/1994 | Goldowsky |
| 5,391,179 A | 2/1995 | Mezzoli |
| 5,417,743 A | 5/1995 | Dauber |
| 5,437,651 A | 8/1995 | Todd et al. |
| 5,449,003 A | 9/1995 | Sugimura |
| 5,449,347 A | 9/1995 | Preen et al. |
| 5,449,584 A | 9/1995 | Banba et al. |
| 5,466,229 A | 11/1995 | Elson et al. |
| 5,492,313 A | 2/1996 | Pan et al. |
| 5,549,584 A | 8/1996 | Gross |
| 5,616,121 A | 4/1997 | McKay |
| 5,634,391 A | 6/1997 | Eady |
| 5,636,643 A * | 6/1997 | Argenta .................. A61F 13/05 602/42 |
| 5,645,081 A | 7/1997 | Argenta et al. |
| 5,676,525 A | 10/1997 | Berner et al. |
| 5,685,214 A | 11/1997 | Neff et al. |
| 5,687,633 A | 11/1997 | Eady |
| 5,693,013 A | 12/1997 | Geuder |
| 5,730,587 A | 3/1998 | Snyder et al. |
| 5,743,170 A | 4/1998 | Pascual et al. |
| 5,759,570 A | 6/1998 | Arnold |
| 5,769,608 A | 6/1998 | Seale |
| 5,785,508 A | 7/1998 | Bolt |
| 5,827,246 A | 10/1998 | Bowen |
| 5,863,184 A | 1/1999 | Juterbock et al. |
| 5,897,296 A | 4/1999 | Yamamoto et al. |
| 5,950,523 A | 9/1999 | Reynolds |
| 6,056,519 A | 5/2000 | Morita et al. |
| 6,068,588 A | 5/2000 | Goldowsky |
| 6,071,267 A | 6/2000 | Zamierowski |
| 6,080,685 A | 6/2000 | Eady |
| 6,102,680 A | 8/2000 | Fraser et al. |
| 6,138,550 A | 10/2000 | Fingar, Jr. et al. |
| 6,142,982 A | 11/2000 | Hunt et al. |
| 6,145,430 A | 11/2000 | Able et al. |
| 6,158,327 A | 12/2000 | Huss |
| 6,162,194 A | 12/2000 | Shipp |
| 6,174,136 B1 | 1/2001 | Kilayko et al. |
| 6,193,658 B1 | 2/2001 | Wendelken et al. |
| 6,227,825 B1 | 5/2001 | Vay |
| 6,230,609 B1 | 5/2001 | Bender et al. |
| 6,231,310 B1 | 5/2001 | Tojo et al. |
| 6,249,198 B1 | 6/2001 | Clark et al. |
| 6,323,568 B1 | 11/2001 | Zabar |
| 6,327,960 B1 | 12/2001 | Heimueller et al. |
| 6,343,539 B1 | 2/2002 | Du |
| 6,413,057 B1 | 7/2002 | Hong et al. |
| 6,514,047 B2 | 2/2003 | Burr et al. |
| 6,540,490 B1 | 4/2003 | Lilie |
| 6,589,028 B1 | 7/2003 | Eckerbom et al. |
| 6,604,908 B1 | 8/2003 | Bryant et al. |
| 6,618,221 B2 | 9/2003 | Gillis et al. |
| 6,623,255 B2 | 9/2003 | Joong et al. |
| 6,626,891 B2 | 9/2003 | Ohmstede |
| 6,638,035 B1 | 10/2003 | Puff |
| 6,652,252 B2 | 11/2003 | Zabar |
| 6,655,257 B1 | 12/2003 | Meyer |
| 6,673,036 B1 | 1/2004 | Britto |
| 6,685,681 B2 | 2/2004 | Lockwood et al. |
| 6,695,823 B1 | 2/2004 | Lina et al. |
| 6,752,794 B2 | 6/2004 | Lockwood et al. |
| 6,755,807 B2 | 6/2004 | Risk, Jr. et al. |
| 6,756,903 B2 | 6/2004 | Omry et al. |
| 6,815,846 B2 | 11/2004 | Godkin |
| 6,823,905 B1 | 11/2004 | Smith et al. |
| 6,877,419 B2 | 4/2005 | Ohrle et al. |
| 6,936,037 B2 | 8/2005 | Bubb et al. |
| 6,951,553 B2 | 10/2005 | Bubb et al. |
| 6,979,324 B2 | 12/2005 | Bybordi et al. |
| 7,022,113 B2 | 4/2006 | Lockwood et al. |
| 7,041,057 B1 | 5/2006 | Faupel et al. |
| 7,108,683 B2 | 9/2006 | Zamierowski |
| 7,128,735 B2 | 10/2006 | Weston |
| 7,151,348 B1 | 12/2006 | Ueda et al. |
| 7,198,046 B1 * | 4/2007 | Argenta .................. A61M 1/91 602/42 |
| 7,361,184 B2 | 4/2008 | Joshi |
| 7,363,850 B2 | 4/2008 | Becker |
| 7,374,409 B2 | 5/2008 | Kawamura |
| 7,381,859 B2 | 6/2008 | Hunt et al. |
| 7,401,703 B2 | 7/2008 | McMichael et al. |
| 7,447,327 B2 | 11/2008 | Kitamura et al. |
| 7,524,315 B2 | 4/2009 | Blott et al. |
| 7,534,927 B2 | 5/2009 | Lockwood et al. |
| 7,550,034 B2 | 6/2009 | Janse Van Rensburg et al. |
| 7,553,306 B1 | 6/2009 | Hunt et al. |
| 7,569,742 B2 | 8/2009 | Haggstrom et al. |
| 7,615,036 B2 | 11/2009 | Joshi et al. |
| 7,625,362 B2 | 12/2009 | Boehringer et al. |
| 7,670,323 B2 | 3/2010 | Hunt et al. |
| 7,699,823 B2 | 4/2010 | Haggstrom et al. |
| 7,700,819 B2 | 4/2010 | Ambrosio et al. |
| 7,708,724 B2 | 5/2010 | Weston |
| 7,722,582 B2 | 5/2010 | Lina et al. |
| 7,758,555 B2 | 7/2010 | Kelch et al. |
| 7,759,537 B2 | 7/2010 | Bishop et al. |
| 7,759,539 B2 | 7/2010 | Shaw et al. |
| 7,775,998 B2 | 8/2010 | Riesinger |
| 7,779,625 B2 | 8/2010 | Joshi et al. |
| 7,785,247 B2 | 8/2010 | Tatum et al. |
| 7,811,269 B2 | 10/2010 | Boynton et al. |
| 7,838,717 B2 | 11/2010 | Haggstrom et al. |

(56) References Cited

U.S. PATENT DOCUMENTS

| | | |
|---|---|---|
| 7,846,141 B2 | 12/2010 | Weston |
| 7,909,805 B2 | 3/2011 | Weston |
| 7,910,791 B2 | 3/2011 | Coffey |
| 7,922,703 B2 | 4/2011 | Riesinger |
| 7,927,319 B2 | 4/2011 | Lawhorn |
| 7,964,766 B2 | 6/2011 | Blott et al. |
| 8,007,257 B2 | 8/2011 | Heaton et al. |
| 8,025,052 B2 | 9/2011 | Matthews et al. |
| 8,034,037 B2 | 10/2011 | Adams et al. |
| 8,061,360 B2 | 11/2011 | Locke et al. |
| 8,062,272 B2 | 11/2011 | Weston |
| 8,062,273 B2 | 11/2011 | Weston |
| 8,062,331 B2 | 11/2011 | Zamierowski |
| 8,080,702 B2 | 12/2011 | Blott et al. |
| 8,097,272 B2 | 1/2012 | Addison |
| 8,105,295 B2 | 1/2012 | Blott et al. |
| 8,118,794 B2 | 2/2012 | Weston |
| 8,152,785 B2 | 4/2012 | Vitaris |
| 8,162,907 B2 | 4/2012 | Heagle |
| 8,186,978 B2 | 5/2012 | Tinholt et al. |
| 8,188,331 B2 | 5/2012 | Barta et al. |
| 8,202,262 B2 | 6/2012 | Lina et al. |
| 8,207,392 B2 | 6/2012 | Haggstrom et al. |
| 8,215,929 B2 | 7/2012 | Shen et al. |
| 8,241,015 B2 | 8/2012 | Lillie et al. |
| 8,241,018 B2 | 8/2012 | Harr |
| 8,241,261 B2 | 8/2012 | Randolph et al. |
| 8,257,327 B2 | 9/2012 | Blott et al. |
| 8,257,328 B2 | 9/2012 | Augustine et al. |
| 8,267,918 B2 | 9/2012 | Johnson et al. |
| 8,282,611 B2 | 10/2012 | Weston |
| 8,294,586 B2 | 10/2012 | Pidgeon et al. |
| 8,303,552 B2 | 11/2012 | Weston |
| 8,308,714 B2 | 11/2012 | Weston et al. |
| 8,317,774 B2 | 11/2012 | Adahan |
| 8,323,264 B2 | 12/2012 | Weston et al. |
| 8,350,116 B2 | 1/2013 | Lockwood et al. |
| 8,363,881 B2 | 1/2013 | Godkin |
| 8,366,690 B2 | 2/2013 | Locke et al. |
| 8,366,692 B2 | 2/2013 | Weston et al. |
| 8,372,049 B2 | 2/2013 | Jaeb et al. |
| 8,372,050 B2 | 2/2013 | Jaeb et al. |
| 8,398,614 B2 | 3/2013 | Blott et al. |
| D679,819 S | 4/2013 | Peron |
| D679,820 S | 4/2013 | Peron |
| 8,409,157 B2 | 4/2013 | Haggstrom et al. |
| 8,409,170 B2 | 4/2013 | Locke et al. |
| 8,414,519 B2 | 4/2013 | Hudspeth et al. |
| 8,425,478 B2 | 4/2013 | Olson |
| 8,444,612 B2 | 5/2013 | Patel et al. |
| 8,449,267 B2 | 5/2013 | Pascual et al. |
| 8,449,509 B2 | 5/2013 | Weston |
| 8,460,255 B2 | 6/2013 | Joshi et al. |
| 8,545,464 B2 | 10/2013 | Weston |
| 8,569,566 B2 | 10/2013 | Blott et al. |
| 8,617,129 B2 | 12/2013 | Hartwell |
| 8,622,981 B2 | 1/2014 | Hartwell et al. |
| 8,628,505 B2 | 1/2014 | Weston |
| 8,641,691 B2 | 2/2014 | Fink et al. |
| 8,663,198 B2 | 3/2014 | Buan et al. |
| 8,663,200 B2 | 3/2014 | Weston et al. |
| 8,715,256 B2 | 5/2014 | Greener |
| 8,734,131 B2 | 5/2014 | McCrone et al. |
| 8,734,425 B2 | 5/2014 | Nicolini |
| 8,764,732 B2 | 7/2014 | Hartwell |
| 8,795,243 B2 | 8/2014 | Weston |
| 8,808,274 B2 | 8/2014 | Hartwell |
| 8,814,841 B2 | 8/2014 | Hartwell |
| 8,827,983 B2 | 9/2014 | Braga et al. |
| 8,829,263 B2 | 9/2014 | Haggstrom et al. |
| 8,834,451 B2 | 9/2014 | Blott et al. |
| 8,843,327 B2 | 9/2014 | Vernon-Harcourt et al. |
| 8,845,603 B2 | 9/2014 | Middleton et al. |
| 8,905,985 B2 | 12/2014 | Allen et al. |
| 8,945,074 B2 | 2/2015 | Buan et al. |
| 8,951,235 B2 | 2/2015 | Allen et al. |
| 8,956,336 B2 | 2/2015 | Haggstrom et al. |
| 8,974,429 B2 | 3/2015 | Gordon et al. |
| 9,061,095 B2 | 6/2015 | Adie et al. |
| 9,067,003 B2 | 6/2015 | Buan et al. |
| 9,084,845 B2 | 7/2015 | Adie et al. |
| 9,192,332 B2 | 11/2015 | Hartwell |
| 9,199,011 B2 | 12/2015 | Locke et al. |
| 9,199,012 B2 | 12/2015 | Vitaris et al. |
| 9,220,822 B2 | 12/2015 | Hartwell |
| 9,220,823 B2 | 12/2015 | Nicolini |
| 9,312,557 B2 | 4/2016 | Zhang et al. |
| 9,314,557 B2 | 4/2016 | Ricci et al. |
| 9,987,402 B2 * | 6/2018 | Hartwell ............... A61B 5/107 |
| 2001/0001278 A1 | 5/2001 | Drevet |
| 2001/0033795 A1 | 10/2001 | Humpheries |
| 2001/0043870 A1 | 11/2001 | Song |
| 2002/0026946 A1 | 3/2002 | McKay |
| 2002/0122732 A1 | 9/2002 | Oh et al. |
| 2002/0164255 A1 | 11/2002 | Burr et al. |
| 2002/0198504 A1 | 12/2002 | Risk, Jr. et al. |
| 2003/0035743 A1 | 2/2003 | Lee et al. |
| 2003/0040687 A1 | 2/2003 | Boynton et al. |
| 2003/0095879 A1 | 5/2003 | Oh et al. |
| 2003/0099558 A1 | 5/2003 | Chang |
| 2003/0108430 A1 | 6/2003 | Yoshida et al. |
| 2003/0110939 A1 | 6/2003 | Able et al. |
| 2003/0133812 A1 | 7/2003 | Puff et al. |
| 2003/0161735 A1 | 8/2003 | Kim et al. |
| 2003/0162071 A1 | 8/2003 | Yasuda |
| 2003/0175125 A1 | 9/2003 | Kwon et al. |
| 2003/0175135 A1 | 9/2003 | Heo et al. |
| 2003/0230191 A1 | 12/2003 | Ohrle et al. |
| 2004/0005222 A1 | 1/2004 | Yoshida et al. |
| 2004/0021123 A1 | 2/2004 | Howell et al. |
| 2004/0064132 A1 | 4/2004 | Boehringer et al. |
| 2004/0066097 A1 | 4/2004 | Kobayashi et al. |
| 2004/0071568 A1 | 4/2004 | Hyeon |
| 2004/0071572 A1 | 4/2004 | Greter |
| 2004/0115076 A1 | 6/2004 | Lilie et al. |
| 2004/0118460 A1 | 6/2004 | Stinson |
| 2004/0126250 A1 | 7/2004 | Tsuchiya et al. |
| 2004/0155741 A1 | 8/2004 | Godin |
| 2004/0156730 A1 | 8/2004 | Lilie et al. |
| 2004/0163713 A1 | 8/2004 | Schulze et al. |
| 2004/0182237 A1 | 9/2004 | Headley et al. |
| 2004/0189103 A1 | 9/2004 | Duncan et al. |
| 2004/0219059 A1 | 11/2004 | Barringer et al. |
| 2005/0031470 A1 | 2/2005 | Lee |
| 2005/0098031 A1 | 5/2005 | Yoon et al. |
| 2005/0100450 A1 | 5/2005 | Bryant et al. |
| 2005/0110190 A1 | 5/2005 | Giardini et al. |
| 2005/0111987 A1 | 5/2005 | Yoo et al. |
| 2005/0123422 A1 | 6/2005 | Lilie |
| 2005/0124966 A1 | 6/2005 | Karpowicz et al. |
| 2005/0129540 A1 | 6/2005 | Puff |
| 2005/0135946 A1 | 6/2005 | Kang et al. |
| 2005/0142007 A1 | 6/2005 | Lee et al. |
| 2005/0142008 A1 | 6/2005 | Jung et al. |
| 2005/0155657 A1 | 7/2005 | Kach et al. |
| 2005/0163635 A1 | 7/2005 | Berwanger et al. |
| 2005/0209560 A1 | 9/2005 | Boukhny et al. |
| 2005/0251117 A1 | 11/2005 | Anderson et al. |
| 2005/0267402 A1 | 12/2005 | Stewart et al. |
| 2005/0271526 A1 | 12/2005 | Chang et al. |
| 2005/0272142 A1 | 12/2005 | Horita |
| 2005/0276706 A1 | 12/2005 | Radue |
| 2006/0009744 A1 | 1/2006 | Erdman et al. |
| 2006/0017332 A1 | 1/2006 | Kang et al. |
| 2006/0018771 A1 | 1/2006 | Song et al. |
| 2006/0019144 A1 | 1/2006 | Hidaka et al. |
| 2006/0024181 A1 | 2/2006 | Kim |
| 2006/0029675 A1 | 2/2006 | Ginther |
| 2006/0039806 A1 | 2/2006 | Becker |
| 2006/0056979 A1 | 3/2006 | Yoo et al. |
| 2006/0056980 A1 | 3/2006 | Yoo et al. |
| 2006/0057000 A1 | 3/2006 | Hyeon |
| 2006/0061024 A1 | 3/2006 | Jung et al. |
| 2006/0073036 A1 | 4/2006 | Pascual et al. |

(56) References Cited

U.S. PATENT DOCUMENTS

| | | |
|---|---|---|
| 2006/0083623 A1 | 4/2006 | Higgins et al. |
| 2006/0110259 A1 | 5/2006 | Puff et al. |
| 2006/0118190 A1 | 6/2006 | Takehana et al. |
| 2006/0122558 A1 | 6/2006 | Sherman et al. |
| 2006/0191575 A1 | 8/2006 | Naesje |
| 2006/0192259 A1 | 8/2006 | Silverbrook |
| 2006/0210411 A1 | 9/2006 | Hyeon |
| 2006/0216165 A1 | 9/2006 | Lee |
| 2006/0222532 A1 | 10/2006 | Lee et al. |
| 2006/0228224 A1 | 10/2006 | Hong et al. |
| 2006/0245947 A1 | 11/2006 | Seto et al. |
| 2006/0251523 A1 | 11/2006 | Lee et al. |
| 2006/0271020 A1 | 11/2006 | Huang et al. |
| 2006/0282174 A1 | 12/2006 | Haines |
| 2006/0282175 A1 | 12/2006 | Haines et al. |
| 2006/0287632 A1 | 12/2006 | Sarangapani |
| 2007/0014837 A1 | 1/2007 | Johnson et al. |
| 2007/0016152 A1 | 1/2007 | Karpowicz et al. |
| 2007/0032741 A1 | 2/2007 | Hibner et al. |
| 2007/0032762 A1 | 2/2007 | Vogel |
| 2007/0032763 A1 | 2/2007 | Vogel |
| 2007/0040454 A1 | 2/2007 | Freudenberger et al. |
| 2007/0041856 A1 | 2/2007 | Hansen et al. |
| 2007/0052144 A1 | 3/2007 | Knirck et al. |
| 2007/0055209 A1 | 3/2007 | Patel et al. |
| 2007/0078444 A1 | 4/2007 | Larsson |
| 2007/0091614 A1 | 4/2007 | Kaisser et al. |
| 2007/0179460 A1 | 8/2007 | Adahan |
| 2007/0196214 A1 | 8/2007 | Bocchiola |
| 2007/0219532 A1 | 9/2007 | Karpowicz et al. |
| 2007/0225663 A1 | 9/2007 | Watt et al. |
| 2007/0256428 A1 | 11/2007 | Unger et al. |
| 2007/0260226 A1 | 11/2007 | Jaeb et al. |
| 2007/0276195 A1 | 11/2007 | Xu et al. |
| 2007/0276309 A1 | 11/2007 | Xu et al. |
| 2007/0282283 A1 | 12/2007 | Kaern et al. |
| 2007/0292286 A1 | 12/2007 | Hell et al. |
| 2007/0295201 A1 | 12/2007 | Dadd |
| 2008/0004549 A1* | 1/2008 | Anderson ............... A61M 1/90 601/6 |
| 2008/0008607 A1 | 1/2008 | Schade et al. |
| 2008/0015526 A1 | 1/2008 | Reiner et al. |
| 2008/0020178 A1 | 1/2008 | Ohrle et al. |
| 2008/0051708 A1 | 2/2008 | Kumar et al. |
| 2008/0071161 A1 | 3/2008 | Jaeb et al. |
| 2008/0071162 A1* | 3/2008 | Jaeb ............... A61M 1/90 600/407 |
| 2008/0071216 A1 | 3/2008 | Locke et al. |
| 2008/0082040 A1 | 4/2008 | Kubler et al. |
| 2008/0089796 A1 | 4/2008 | Schade et al. |
| 2008/0094753 A1 | 4/2008 | Brodkin et al. |
| 2008/0110336 A1 | 5/2008 | Cresswell et al. |
| 2008/0125697 A1 | 5/2008 | Gao |
| 2008/0125698 A1 | 5/2008 | Gerg et al. |
| 2008/0191399 A1 | 8/2008 | Chang |
| 2008/0208147 A1* | 8/2008 | Argenta ............... A61H 7/001 604/290 |
| 2008/0211435 A1 | 9/2008 | Imagawa |
| 2008/0228526 A1* | 9/2008 | Locke ............... A61H 9/0057 601/6 |
| 2008/0240942 A1 | 10/2008 | Heinrich et al. |
| 2008/0260551 A1 | 10/2008 | Simmons |
| 2008/0267797 A1 | 10/2008 | Hell et al. |
| 2008/0281281 A1 | 11/2008 | Meyer et al. |
| 2008/0306456 A1 | 12/2008 | Riesinger |
| 2008/0310980 A1 | 12/2008 | Ramsdorf et al. |
| 2009/0008306 A1 | 1/2009 | Cicchello et al. |
| 2009/0012441 A1 | 1/2009 | Mulligan |
| 2009/0012483 A1* | 1/2009 | Blott ............... A61M 27/00 604/315 |
| 2009/0012501 A1* | 1/2009 | Boehringer ............... A61M 1/966 604/543 |
| 2009/0028733 A1 | 1/2009 | Duwel |
| 2009/0030383 A1 | 1/2009 | Larsen et al. |
| 2009/0030402 A1* | 1/2009 | Adahan ............... A61M 1/962 15/300.1 |
| 2009/0053081 A1 | 2/2009 | Griffiths |
| 2009/0054855 A1* | 2/2009 | Blott ............... A61M 35/30 604/290 |
| 2009/0060750 A1 | 3/2009 | Chen et al. |
| 2009/0071551 A1 | 3/2009 | Chalich |
| 2009/0081049 A1 | 3/2009 | Tian et al. |
| 2009/0087323 A1 | 4/2009 | Blakey et al. |
| 2009/0114293 A1 | 5/2009 | Kanai et al. |
| 2009/0116712 A1 | 5/2009 | Al-Moosawi et al. |
| 2009/0123513 A1 | 5/2009 | Greener |
| 2009/0125004 A1 | 5/2009 | Shen et al. |
| 2009/0129955 A1 | 5/2009 | Schubert |
| 2009/0129986 A1 | 5/2009 | Wimberger-Friedl et al. |
| 2009/0148320 A1 | 6/2009 | Lucas |
| 2009/0149821 A1 | 6/2009 | Scherson et al. |
| 2009/0157016 A1* | 6/2009 | Adahan ............... F04B 43/04 604/315 |
| 2009/0166411 A1 | 7/2009 | Kramer et al. |
| 2009/0169402 A1 | 7/2009 | Stenberg |
| 2009/0177051 A1 | 7/2009 | Arons et al. |
| 2009/0206778 A1 | 8/2009 | Roh et al. |
| 2009/0227969 A1 | 9/2009 | Jaeb et al. |
| 2009/0234306 A1 | 9/2009 | Vitaris |
| 2009/0270833 A1 | 10/2009 | DeBelser et al. |
| 2009/0292264 A1 | 11/2009 | Hudspeth et al. |
| 2009/0299251 A1 | 12/2009 | Buan |
| 2009/0299306 A1 | 12/2009 | Buan |
| 2009/0304534 A1 | 12/2009 | Richter |
| 2009/0306580 A1* | 12/2009 | Blott ............... A61M 1/92 604/290 |
| 2009/0312723 A1 | 12/2009 | Blott et al. |
| 2009/0312725 A1 | 12/2009 | Braga |
| 2009/0315684 A1 | 12/2009 | Sacco et al. |
| 2010/0030132 A1* | 2/2010 | Niezgoda ............... A61M 1/73 604/289 |
| 2010/0036367 A1 | 2/2010 | Krohn |
| 2010/0042059 A1 | 2/2010 | Pratt et al. |
| 2010/0068820 A1 | 3/2010 | Meathrel et al. |
| 2010/0098566 A1 | 4/2010 | Kang |
| 2010/0125258 A1 | 5/2010 | Coulthard et al. |
| 2010/0126484 A1 | 5/2010 | Skell et al. |
| 2010/0191126 A1 | 7/2010 | Al-Moosawi et al. |
| 2010/0211030 A1 | 8/2010 | Turner et al. |
| 2010/0244780 A1 | 9/2010 | Turner et al. |
| 2010/0249733 A9 | 9/2010 | Blott et al. |
| 2010/0265649 A1 | 10/2010 | Singh et al. |
| 2010/0268179 A1 | 10/2010 | Kelch et al. |
| 2010/0280435 A1 | 11/2010 | Raney et al. |
| 2010/0305526 A1 | 12/2010 | Robinson et al. |
| 2010/0324510 A1 | 12/2010 | Andresen et al. |
| 2011/0000069 A1 | 1/2011 | Ramsdorf et al. |
| 2011/0004172 A1 | 1/2011 | Eckstein et al. |
| 2011/0020588 A1 | 1/2011 | Shimizu et al. |
| 2011/0028921 A1 | 2/2011 | Hartwell et al. |
| 2011/0054423 A1 | 3/2011 | Blott et al. |
| 2011/0077605 A1 | 3/2011 | Karpowicz et al. |
| 2011/0081267 A1 | 4/2011 | McCrone et al. |
| 2011/0098600 A1 | 4/2011 | Matsumura et al. |
| 2011/0103984 A1 | 5/2011 | Santa |
| 2011/0118683 A1 | 5/2011 | Weston |
| 2011/0130712 A1 | 6/2011 | Topaz |
| 2011/0171044 A1 | 7/2011 | Flanigan |
| 2011/0176945 A1 | 7/2011 | Drevet |
| 2011/0176946 A1 | 7/2011 | Drevet |
| 2011/0184341 A1 | 7/2011 | Baker et al. |
| 2011/0202220 A1 | 8/2011 | Seta et al. |
| 2011/0224631 A1 | 9/2011 | Simmons et al. |
| 2011/0229352 A1 | 9/2011 | Timmer |
| 2011/0236265 A1 | 9/2011 | Hasui et al. |
| 2011/0236277 A1 | 9/2011 | Lee et al. |
| 2011/0251569 A1 | 10/2011 | Turner et al. |
| 2011/0257572 A1 | 10/2011 | Locke et al. |
| 2011/0282310 A1* | 11/2011 | Boehringer ............... A61M 1/82 604/319 |
| 2012/0035469 A1 | 2/2012 | Whelan et al. |
| 2012/0041399 A1 | 2/2012 | Blott et al. |
| 2012/0259299 A1 | 10/2012 | Ryu et al. |

(56) References Cited

U.S. PATENT DOCUMENTS

| | | |
|---|---|---|
| 2012/0271256 A1 | 10/2012 | Locke et al. |
| 2013/0085462 A1 | 4/2013 | Nip et al. |
| 2013/0090613 A1 | 4/2013 | Kelch et al. |
| 2013/0116635 A1 | 5/2013 | Fleischmann |
| 2013/0123755 A1 | 5/2013 | Locke et al. |
| 2013/0138054 A1 | 5/2013 | Fleischmann |
| 2013/0144230 A1 | 6/2013 | Wu et al. |
| 2013/0144235 A1 | 6/2013 | Augustine et al. |
| 2013/0150813 A1 | 6/2013 | Gordon et al. |
| 2013/0150814 A1 | 6/2013 | Buan |
| 2013/0165878 A1 | 6/2013 | Heagle |
| 2013/0267917 A1 | 10/2013 | Pan et al. |
| 2013/0274688 A1 | 10/2013 | Weston |
| 2013/0331822 A1 | 12/2013 | Patel et al. |
| 2014/0114268 A1 | 4/2014 | Auguste et al. |
| 2014/0163490 A1 | 6/2014 | Locke et al. |
| 2014/0163493 A1 | 6/2014 | Weston et al. |
| 2014/0228791 A1 | 8/2014 | Hartwell |
| 2014/0276487 A1 | 9/2014 | Locke et al. |
| 2014/0316359 A1 | 10/2014 | Collinson et al. |
| 2015/0025482 A1 | 1/2015 | Begin et al. |
| 2015/0032035 A1 | 1/2015 | Banwell et al. |
| 2015/0051560 A1 | 2/2015 | Askem |
| 2015/0073363 A1 | 3/2015 | Kelch et al. |
| 2015/0174304 A1 | 6/2015 | Askem et al. |
| 2015/0217032 A1 | 8/2015 | Allen et al. |
| 2016/0166741 A1 | 6/2016 | Nicolini |
| 2020/0171217 A9 | 6/2020 | Braga et al. |

FOREIGN PATENT DOCUMENTS

| | | | |
|---|---|---|---|
| CN | 101516431 A | 8/2009 | |
| CN | 101616700 A | 12/2009 | |
| CN | 101676563 A | 3/2010 | |
| CN | 201953601 U | 8/2011 | |
| CN | 103221077 A | 7/2013 | |
| DE | 102005007016 A1 | 8/2006 | |
| EP | 0208395 A1 | 1/1987 | |
| EP | 0411564 A2 | 2/1991 | |
| EP | 0578999 A1 | 1/1994 | |
| EP | 0604953 A1 | 7/1994 | |
| EP | 0759521 A1 | 2/1997 | |
| EP | 0775825 A2 | 5/1997 | |
| EP | 0793019 A2 | 9/1997 | |
| EP | 0809028 A2 | 11/1997 | |
| EP | 0898076 A1 | 2/1999 | |
| EP | 1114933 A2 | 7/2001 | |
| EP | 1153218 A1 | 11/2001 | |
| EP | 0909895 B1 | 12/2002 | |
| EP | 0708620 B1 | 5/2003 | |
| EP | 0993317 B1 | 9/2003 | |
| EP | 1406020 A2 | 4/2004 | |
| EP | 1430588 A2 | 6/2004 | |
| EP | 1449971 A1 | 8/2004 | |
| EP | 1476217 A2 | 11/2004 | |
| EP | 1554737 A1 | 7/2005 | |
| EP | 1556942 A1 | 7/2005 | |
| EP | 1469580 B1 | 12/2005 | |
| EP | 1757809 A1 | 2/2007 | |
| EP | 1850005 A1 | 10/2007 | |
| EP | 1460270 B1 | 6/2008 | |
| EP | 1791579 B1 | 7/2009 | |
| EP | 2145636 A2 | 1/2010 | |
| EP | 2161448 A1 | 3/2010 | |
| EP | 1932481 B1 | 6/2010 | |
| EP | 2216573 A1 | 8/2010 | |
| EP | 2253353 A1 | 11/2010 | |
| EP | 2302127 A1 | 3/2011 | |
| EP | 1956242 B1 | 4/2011 | |
| EP | 2366721 A1 | 9/2011 | |
| EP | 2462908 A1 | 6/2012 | |
| EP | 2544642 B1 | 1/2015 | |
| EP | 2648668 A4 | 1/2015 | |
| EP | 2836711 A1 | 2/2015 | |
| EP | 2109472 B1 | 8/2015 | |
| EP | 2254612 B1 | 10/2019 | |
| FR | 1163907 A | 10/1958 | |
| GB | 1039145 A | 8/1966 | |
| GB | 1220857 A | 1/1971 | |
| GB | 2235877 A | 3/1991 | |
| GB | 2273133 A | 6/1994 | |
| GB | 2306580 A | 5/1997 | |
| GB | 2342584 A | 4/2000 | |
| GB | 2418738 A | 4/2006 | |
| GB | 2433298 A | 6/2007 | |
| JP | 2000105011 A | 4/2000 | |
| JP | 2000220570 A | 8/2000 | |
| JP | 2000300662 A | 10/2000 | |
| JP | 2001241382 A | 9/2001 | |
| JP | 2001286807 A | 10/2001 | |
| JP | 2006233925 A | 9/2006 | |
| JP | 2008183244 A | 8/2008 | |
| JP | 2008194294 A | 8/2008 | |
| JP | 2010185458 A | 8/2010 | |
| JP | 2013514871 A | 5/2013 | |
| WO | WO-8707683 A2 | 12/1987 | |
| WO | WO-9420041 A1 | 9/1994 | |
| WO | WO-9421312 A2 | 9/1994 | |
| WO | WO-9605873 A1 | 2/1996 | |
| WO | WO-9819068 A1 | 5/1998 | |
| WO | WO-0000743 A1 | 1/2000 | |
| WO | WO-0007653 A1 | 2/2000 | |
| WO | WO-0021586 A1 | 4/2000 | |
| WO | WO-0022298 A2 | 4/2000 | |
| WO | WO-0049968 A2 | 8/2000 | |
| WO | WO-0056378 A1 | 9/2000 | |
| WO | WO-0061206 A1 | 10/2000 | |
| WO | WO-0079154 A2 | 12/2000 | |
| WO | WO-0116488 A1 | 3/2001 | |
| WO | WO-0137922 A2 | 5/2001 | |
| WO | WO-0179693 A2 | 10/2001 | |
| WO | WO-02087058 A1 | 10/2002 | |
| WO | WO-02090772 A1 | 11/2002 | |
| WO | WO-03005943 A2 * | 1/2003 | .......... A61M 1/0027 |
| WO | WO-03057307 A1 | 7/2003 | |
| WO | WO-03085810 A1 | 10/2003 | |
| WO | WO-03099356 A2 | 12/2003 | |
| WO | WO-03101508 A2 | 12/2003 | |
| WO | WO-2004007960 A1 | 1/2004 | |
| WO | WO-2004037334 A1 | 5/2004 | |
| WO | WO-2004081421 A2 | 9/2004 | |
| WO | WO-2005001287 A1 | 1/2005 | |
| WO | WO-2005009488 A2 | 2/2005 | |
| WO | WO-2005046760 A1 | 5/2005 | |
| WO | WO-2005046761 A1 | 5/2005 | |
| WO | WO-2005046762 A1 | 5/2005 | |
| WO | WO-2005105180 A1 | 11/2005 | |
| WO | WO-2005123170 A1 | 12/2005 | |
| WO | WO-2006046060 A2 | 5/2006 | |
| WO | WO-2006052745 A2 * | 5/2006 | .......... A61M 1/0011 |
| WO | WO-2006052839 A2 | 5/2006 | |
| WO | WO-2006058801 A1 | 6/2006 | |
| WO | WO-2006059098 A1 | 6/2006 | |
| WO | WO-2006062276 A1 | 6/2006 | |
| WO | WO-2006069875 A2 | 7/2006 | |
| WO | WO-2006069884 A1 | 7/2006 | |
| WO | WO-2006069885 A1 | 7/2006 | |
| WO | WO-2006092333 A1 | 9/2006 | |
| WO | WO-2006111775 A1 | 10/2006 | |
| WO | WO-2006117207 A1 | 11/2006 | |
| WO | WO-2006122268 A2 | 11/2006 | |
| WO | WO-2007019038 A2 | 2/2007 | |
| WO | WO-2007049876 A1 | 5/2007 | |
| WO | WO-2007055642 A1 | 5/2007 | |
| WO | WO-2007067359 A2 | 6/2007 | |
| WO | WO-2007087811 A1 | 8/2007 | |
| WO | WO-2007092397 A2 | 8/2007 | |
| WO | WO-2007113597 A2 | 10/2007 | |
| WO | WO-2008013896 A2 | 1/2008 | |
| WO | WO-2008027449 A2 | 3/2008 | |
| WO | WO-2008031418 A2 | 3/2008 | |
| WO | WO-2008036345 A1 | 3/2008 | |
| WO | WO-2008039223 A1 | 4/2008 | |
| WO | WO-2008039314 A2 | 4/2008 | |

(56) References Cited

FOREIGN PATENT DOCUMENTS

| | | |
|---|---|---|
| WO | WO-2008048481 A2 | 4/2008 |
| WO | WO-2008049029 A2 | 4/2008 |
| WO | WO-2008100440 A1 | 8/2008 |
| WO | WO-2008110022 A2 | 9/2008 |
| WO | WO-2008135997 A2 | 11/2008 |
| WO | WO-2008154158 A2 | 12/2008 |
| WO | WO-2009019415 A2 | 2/2009 |
| WO | WO-2009047524 A2 | 4/2009 |
| WO | WO-2009066104 A1 | 5/2009 |
| WO | WO-2009066105 A1 | 5/2009 |
| WO | WO-2009071924 A1 | 6/2009 |
| WO | WO-2009089390 A2 | 7/2009 |
| WO | WO-2009095170 A2 | 8/2009 |
| WO | WO-2009103031 A1 | 8/2009 |
| WO | WO-2009124100 A1 | 10/2009 |
| WO | WO-2009124125 A2 | 10/2009 |
| WO | WO-2009126103 A1 | 10/2009 |
| WO | WO-2009146441 A1 | 12/2009 |
| WO | WO-2009151645 A2 | 12/2009 |
| WO | WO-2009156984 A2 | 12/2009 |
| WO | WO-2009158128 A2 | 12/2009 |
| WO | WO-2010017484 A2 | 2/2010 |
| WO | WO-2010021783 A1 | 2/2010 |
| WO | WO-2010033613 A1 | 3/2010 |
| WO | WO-2010033769 A1 | 3/2010 |
| WO | WO-2010039481 A1 | 4/2010 |
| WO | WO-2010051068 A1 | 5/2010 |
| WO | WO-2010051418 A2 | 5/2010 |
| WO | WO-2010072349 A1 * | 7/2010 .......... A61M 1/0023 |
| WO | WO-2010093753 A1 | 8/2010 |
| WO | WO-2010126444 A1 | 11/2010 |
| WO | WO-2010142959 A2 | 12/2010 |
| WO | WO-2010147533 A1 | 12/2010 |
| WO | WO-2011087871 A3 | 10/2011 |
| WO | WO-2011135285 A1 | 11/2011 |
| WO | WO-2011135286 A1 | 11/2011 |
| WO | WO-2011135287 A1 | 11/2011 |
| WO | WO-2011144888 A1 | 11/2011 |
| WO | WO-2012038724 A1 | 3/2012 |
| WO | WO-2012131237 A1 | 10/2012 |
| WO | WO-2012140378 A1 | 10/2012 |
| WO | WO-2012143665 A1 | 10/2012 |
| WO | WO-2013010907 A1 | 1/2013 |
| WO | WO-2013064852 A1 | 5/2013 |
| WO | WO-2013083080 A1 | 6/2013 |
| WO | WO-2013118447 A1 | 8/2013 |
| WO | WO-2013140255 A1 | 9/2013 |
| WO | WO-2013149078 A1 | 10/2013 |
| WO | WO-2014008348 A2 | 1/2014 |
| WO | WO-2014016759 A1 | 1/2014 |
| WO | WO-2014020440 A1 | 2/2014 |
| WO | WO-2014020443 A2 | 2/2014 |
| WO | WO-2014108476 A1 | 7/2014 |
| WO | WO-2014113253 A1 | 7/2014 |
| WO | WO-2015022334 A1 | 2/2015 |
| WO | WO-2015022340 A1 | 2/2015 |

OTHER PUBLICATIONS

Annex to the Communication, the Opposition of European Patent No. 2773383, mailed on Sep. 13, 2019, 17 pages.
Appeal Decision for Japanese Patent Application No. 2013528768, mailed on Jul. 14, 2017, 20 pages.
Brief Communication—Letter from the Opponent, re the Opposition of European Patent No. 2773383, dated Mar. 24, 2021, 4 pages.
Brief Communication—Letter from the Proprietor of the Patent, re the Opposition of European Patent No. 2773383, dated Mar. 24, 2021, 25 pages.
Brief Communication, Letter from the Proprietor for Opposition of European Patent No. EP 2237724, mailed on Jun. 19, 2017, 24 pages.
Brief Communication, Letter from the Proprietor for Opposition of European Patent No. EP2237724, mailed on Aug. 21, 2018, 5 pages.
Brief Communication of the Opposition Proceedings for European Patent No. 3326656, mailed on Aug. 25, 2021, 34 pages.
British Standards Institution, "Sterilization of medical devices and packaging," retrieved from URL: https://shop.bsigroup.com/en/Browse-By-Subject/Medical-Device-Standards/Sterilization-of-medical-devices-and-packaging/ on Mar. 12, 2020, 1 page.
Communication of further notices of opposition pursuant to Rule 79(2) EPC for the European Patent No. 3146986, mailed on Aug. 20, 2020, 2 pages.
Consolidated List of Cited Opposition Documents of the European Patent No. 2773383, dated Jan. 23, 2020, 1 page.
Decision to Maintain the European Patent in Amended Form (Art, 101 (3)(a) EPC) for European Patent No. 2237724, mailed on Sep. 19, 2019, 2 pages.
Diels K., et al., "Leybold Vacuum Handbook," Pergamon Press, 1966, 10 pages.
Extent of the Opposition and Request for European Patent No. 3326656, mailed on Feb. 12, 2021, 58 pages.
Grounds for the Decision and Annex to the Communication, Opposition of European Patent No. 2237724, dated Jan. 7, 2019, 78 pages.
Information about the result of oral proceedings for European Patent No. 2773383, dated May 19, 2021, 2 pages.
International Preliminary Report on Patentability for Application No. PCT/GB2008/050917, mailed on Jun. 8, 2010, 7 pages.
International Preliminary Report on Patentability for Application No. PCT/GB2011/051745, mailed on Mar. 26, 2013, 7 pages.
International Preliminary Report on Patentability re PCT Application No. PCT/US2011/059016 dated Apr. 29, 2014, 12 pages.
International Search Report and Written Opinion for Application No. PCT/IB2011/002943, mailed on Jan. 28, 2013, 24 pages.
International Search Report and Written Opinion for Application No. PCT/US2011/059016, mailed on Apr. 23, 2014, 20 pages.
International Search Report for Application No. PCT/GB2008/050917, mailed on Jan. 14, 2009, 4 pages.
International Search Report for Application No. PCT/GB2011/051745, mailed on Feb. 2, 2012, 5 pages.
Invitation to Pay Additional Fees and Partial Search Report for Application No. PCT/US2011/059016, mailed on Feb. 17, 2014, 7 pages.
KCI, Inc., "Acti V.A.C. Therapy System," User Manual, Sep. 2007, 64 pages.
KCI Licensing, Inc., "V.A.C. Via™—Negative Pressure Wound Therapy System," 7-Day V.A.C.® Therapy System, Instructions for Use, 360063 Rev B, Aug. 2010, 24 pages.
KCI USA Inc., "SNAP™ Therapy System," Instructions for Use, SNAP™ Therapy Cartridge, Jul. 2016, 2 pages.
Kendall ULTEC Hydrocolloid Dressing (4x4"), Product Ordering Page, web page downloaded on Jul. 13, 2014, 1 page.
Letter relating to the Appeal Procedure for the Opposition of the European Patent No. 2618860, mailed on Dec. 23, 2019, 5 pages.
Martin L.H., et al., "A Manual of Vacuum Practice," Melbourne University Press, first published 1947, reprinted 1948, 12 pages.
Matsunaga K., et al., "Gas Permeability of Thermoplastic Polyurethane Elastomers," Polymer Journal, Jun. 2005, vol. 37, No. 6, pp. 413-417.
Morcos A.C., "Voice Coil Actuators & Their Use in Advanced Motion Control Systems," Motion, Jul./Aug. 1995, pp. 25-27.
"SNAP™—Wound Care System," Instructions for Use (L20897), Dec. 9, 2007, 16 pages.
Notice of Communication of amended entries concerning the representative (R. 143(1)(h) EPC) and enclosed letter from the proprietor of the patent dated Jan. 8, 2021 for the European Patent No. 3146986, mailed on Jan. 20, 2021, 6 pages.
Notice of Opposition—Statement of Facts and Arguments for the European Patent No. 2618860, mailed on Aug. 26, 2016, 9 pages.
Notice of Opposition—Statement of Facts and Evidence for the European Patent No. 2773383, dated Dec. 28, 2018, 20 pages.
Notice of Opposition—Statement of Facts and Evidence of the European Patent No. 2237724, dated Dec. 30, 2016, 15 pages.
Notice of Opposition to a European Patent No. 2618860, dated Mar. 16, 2016, 5 pages.

(56) References Cited

OTHER PUBLICATIONS

Observations filed by Third Party for the European Patent No. 2773383, mailed on Jan. 28, 2020, 7 pages.
Opponent Arguments for the European Patent No. EP2773383, dated Jan. 28, 2020, 25 pages.
Opponent's Statement of Facts and Arguments for the European Patent No. 3146986, mailed on Jul. 30, 2020, 6 pages.
Opponent Submissions Prior to Oral Proceedings for Opposition to European Patent No. 2618860, dated Sep. 14, 2017, 4 pages.
Opponent's Written Submission in Preparation for the Oral Proceedings, opposition of the European Patent No. 2773383, dated Mar. 16, 2020, 8 pages.
Opponent's Written Submission in Preparation for the Oral Proceedings, Opposition of the European Patent No. 2237724, dated Aug. 10, 2018, 14 pages.
Opposition—Statement of Facts and Evidence for Opposition for the European Patent No. 2618860, filed on Mar. 16, 2016, 9 pages.
Opposition by KCI Licensing Inc. to EP2708216 Smith & Nephew Inc., Submitted as Evidence in Support of tile Appeal re European Patent No. 2618860, dated Apr. 5, 2018, 5 pages.
Oral Proceeding Minutes, Decision Rejecting the Opposition, and Grounds of Decision, re European Patent No. EP2618860, dated Jan. 19, 2018, 11 pages.
Park S.M., et al., "Design and Analysis of VCA for Fuel Pump in Automobile," World of Academy of Science, Engineering and Technology, vol. 80, 2011, pp. 573-576.
Patentee Final Written Submissions in Advance of Oral Proceedings for Opposition to European Patent No. 2618860, dated Sep. 13, 2017, 4 pages.
Preliminary Opinion of the Opposition Division for the European Patent No. 2618860, mailed on Dec. 22, 2016, 5 pages.
Proprietor Arguments for the European Patent No. EP2773383, dated Jan. 28, 2020, 32 pages.
Proprietor Reply to Statement of Opponent's Grounds of Appeal, re European Patent No. 2618860, dated Sep. 28, 2018, 38 pages.
Proprietor's Written Submission in Preparation for the Oral Proceedings, opposition of European Patent No. 2773383, dated Mar. 18, 2020, 9 pages.
Protz K., "Modern Wound Dressings Support the Healing Process," Wound care: Indications and Application, Geriatrie Journal, Apr. 2005, pp. 3333-3339 (17 pages with English translation).
Rangwala A.S., "Reciprocating Machinery Dynamics," New Age International Publishers, ISBN:81-224-1813-9, 2006, 6 pages.
Reply of the Patent Proprietor to the Notice of the Opposition, the Opposition of European Patent No. 2773383, mailed on Jun. 3, 2019, 11 pages.
Reply of the Patent Proprietor to the Notice(s) of Opposition for European Patent No. EP2237724, dated May 31, 2017, 9 pages.
SNAP™ Therapy System, "Monograph," KCI, 2 pages.
Statement of Opponent's Grounds of Appeal for European Patent No. EP2618860, dated May 18, 2018, 4 pages.
Summons to attend oral proceedings pursuant to Rule 115(1) EPC for European Patent No. 2773383, mailed on Sep. 30, 2020, 19 pages.
Summons to attend oral proceedings pursuant to Rule 115(1) EPC for the European Patent No. 3146986, mailed on Apr. 19, 2021, 10 pages.
Termination of the Opposition Proceedings with Maintenance for European Patent No. 2237724, mailed on Sep. 13, 2019, 1 page.
The Constructor, "Reciprocating Pump—Components, Working and Uses," Retrieved from https://theconstructor.org/practical-guide/reciprocating-pumpcomponents-working-uses/2914/ on Jan. 21, 2020, 4 pages.
The Free Dictionary, "Volume," The American Heritage Dictionary of the English Language, Retrieved from http://www.thefreedictionary.com/volume, Fourth Edition, 2000, 3 pages.
Wikipedia, "Pump," retrieved from https://en.wikipedia.org/wiki/Pump on Mar. 13, 2020, 11 pages.
Written Submission by the Opponent for Opposition of European Patent No. EP2773383, dated Jul. 22, 2020, 2 pages.
Written Submission by the Proprietor for Opposition of European Patent No. EP2773383, dated Jul. 22, 2020, 15 pages.
Board of Appeal—Letter of the opponent dated May 26, 2023 for European Patent No. 3326656, mailed on Jun. 1, 2023, 60 pages.
Board of Appeal—Letter of the Patent Proprietor dated Dec. 7, 2022 for European Patent No. 2773383, mailed on Dec. 13, 2022, 6 pages.
Brief Communication—Letter from the opponent of the Patent, re the Opposition for European Patent No. 3146986, dated Feb. 3, 2022, 2 pages.
Brief Communication—Letter from the opponent of the Patent, re the Opposition for European Patent No. 3146986, dated Jan. 26, 2022, 4 pages.
Brief Communication—Letter from the Opponent, re the Opposition of European Patent No. 3326656, dated Oct. 14, 2021, 41 pages.
Brief Communication—Letter from the Opposition Division Aug. 29, 2022, for European Patent No. 3326656, mailed on Aug. 29, 2022, 2 pages.
Brief Communication—Letter from the Proprietor of the Patent, re the Opposition for European Patent No. 3146986, dated Dec. 15, 2021, 7 pages.
Brief Communication—Letter from the Proprietor of the Patent, re the Opposition for Simmons & Simmons for European Patent No. 3146986, dated Feb. 7, 2022, 2 pages.
Brief Communication—Letter of the Opponent of Aug. 19, 2022, for European Patent No. 3326656, mailed on Aug. 24, 2022, 26 pages.
Brief Communication of the Opposition Proceedings for European Patent No. 3326656, mailed on Jul. 14, 2022, 11 pages.
Communication of the Board of Appeal for European Patent No. 2618860, mailed May 4, 2023, 4 pages.
Decision by a different Opposition Division for European Application No. 11802142.7, mailed on Sep. 24, 2021, 22 pages.
Decision by Opposition Division re the Opposition of European Patent No. 2773383, revoking a patent with claims essentially corresponding to the claims presented in the new requests dated Sep. 24, 2021, 22 pages.
Decision revoking the European Patent (Art. 101 (3)(b) EPC) for European Patent No. 2773383, mailed on Sep. 24, 2021, 56 pages.
Dempsey D.J., "Sterilization of Medical Devices: A Review," Journal of Biomaterials Applications, Jan. 1989, vol. 3, pp. 454-523.
Hoxey E., "Sterilization—Regulatory Requirements and Supporting Standards," BSI National Standards Body, Medical Device White Paper Series, Publication Date Unknown, 27 pages.
Information about the result of oral proceedings for European Application No. 17203441.5, mailed on Sep. 13, 2022, 2 pages.
Interlocutory Decision in Opposition and Accompanying Items for European Patent No. 3146986, mailed on Feb. 23, 2022, 28 pages.
Letter of the Opponent for the European Patent No. 2773383, mailed on Jun. 15, 2022, 57 pages.
Maintenance of the patent with the documents specified in the final decision, re the opposition of European patent No. EP3146986, mailed on Jun. 7, 2022, 1 page.
Opponent's Written Submission in Preparation for the Oral Proceedings, the Opposition of European Patent No. 3146986, dated Dec. 7, 2021, 1 page.
Proprietor's Written Submission in the Opposition Proceedings for European Patent No. 3326656, dated Jul. 13, 2022, 65 pages.
Statement of Grounds of Appeal filed by proprietor for European patent No. 2773383, mailed on Feb. 2, 2022, 53 pages.
Statement of Grounds of Appeal for European Patent No. 3326656, mailed on Feb. 16, 2023, 125 pages.
Summons to Attend Oral Proceedings pursuant to Rule 115(1) for European Patent No. 3326656, mailed on Dec. 16, 2021, 17 pages.
Summons to Attend Oral Proceedings pursuant to rule 115(1) EPC for Application No. 11802142.7, mailed on Jun. 3, 2020, 20 pages.
Termination of the Opposition Proceedings with Maintenance of European Patent No. 2618860, dated Jul. 3, 2023, 1 page.
Termination of the Opposition Proceedings with Maintenance of European Patent No. 3146986, dated Jul. 8, 2022, 1 page.
Transmittal of decision summons for the Opposition of European Patent No. EP3326656, mailed on Oct. 6, 2022, 27 pages.

(56) References Cited

OTHER PUBLICATIONS

Withdrawal of an Appeal—Letter to EPO for European Patent No. 2618860, mailed Jun. 28, 2023, 3 pages.

\* cited by examiner

APPARATUS AND METHOD FOR WOUND VOLUME MEASUREMENT

CROSS-REFERENCE TO RELATED APPLICATIONS

This application is a continuation of U.S. patent application Ser. No. 15/994,818, filed on May 31, 2018, which is a continuation of U.S. patent application Ser. No. 14/946,468, filed on Nov. 19, 2015 and now U.S. Pat. No. 9,987,402, which is a continuation of U.S. patent application Ser. No. 14/455,200, filed Aug. 8, 2014 and now U.S. Pat. No. 9,192,332, which is a division of U.S. application Ser. No. 12/746,492, filed Jun. 4, 2010 and now U.S. Pat. No. 8,814,841, which is a U.S. national stage application of International Patent Application No. PCT/GB2008/050917, filed on Oct. 7, 2008, which claims the benefit of U.K. Application No. GB 0723855.3, filed on Dec. 6, 2007; the disclosure of each of which is hereby incorporated by reference in its entirety.

The present invention relates to apparatus and a method for the measurement of wound volume to assess progress of wound healing particularly, though not exclusively, during topical negative pressure (TNP) therapy.

There is much prior art available relating to the provision of apparatus and methods of use thereof for the application of TNP therapy to wounds together with other therapeutic processes intended to enhance the effects of the TNP therapy. Examples of such prior art include those listed and briefly described below.

TNP therapy assists in the closure and healing of wounds by reducing tissue oedema; encouraging blood flow and granulation of tissue; removing excess exudates and may reduce bacterial load and thus, infection to the wound. Furthermore, TNP therapy permits less outside disturbance of the wound and promotes more rapid healing.

In our co-pending International patent application, WO 2004/037334, apparatus, a wound dressing and a method for aspirating, irrigating and cleansing wounds are described. In very general terms, this invention describes the treatment of a wound by the application of topical negative pressure (TNP) therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In our co-pending International patent application, WO 2005/04670, apparatus, a wound dressing and a method for cleansing a wound using aspiration, irrigation and cleansing wounds are described. Again, in very general terms, the invention described in this document utilises similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound.

In our co-pending International patent application, WO 2005/105180, apparatus and a method for the aspiration, irrigation and/or cleansing of wounds are described. Again, in very general terms, this document describes similar apparatus to the two previously mentioned documents hereinabove but with the additional step of providing means for the supply and application of physiologically active agents to the wound site/dressing to promote wound healing.

The content of the above references is included herein by reference.

However, the above apparatus and methods are generally only applicable to a patient when hospitalised as the apparatus is complex, needing people having specialist knowledge in how to operate and maintain the apparatus, and also relatively heavy and bulky, not being adapted for easy mobility outside of a hospital environment by a patient, for example.

Some patients having relatively less severe wounds which do not require continuous hospitalisation, for example, but whom nevertheless would benefit from the prolonged application of TNP therapy, could be treated at home or at work subject to the availability of an easily portable and maintainable TNP therapy apparatus.

One particular area of wound therapy which is desirable is to monitor the volume of a wound during its treatment such as, for example, at dressing change time so as to be able to quantify the healing process. However, there are presently no simple and/or accurate tools with which to make this assessment of wound volume.

Methods which have been used have include measuring the length, width and depth of a wound and making some assessment from the dimensions but this is very inaccurate; Taking a tracing around the wound, calculating the area and taking depth measurements; filling the wound with a filler and measuring the wound volume based on a known density of the filler; and photographic methods. All of these prior methods involve making calculated guesses resulting in inaccurate volume figures or are time consuming or are rather impractical.

Desirably, wound volume should be measured when a dressing is changed at, for example, every few days so as to keep a continuous record of progress.

Whatever method was used it would result in the figures having to be stored in a file, for example, and generally not with the patient being treated.

It is an aim of the present invention to at least partly mitigate the above-mentioned problems.

According to a first aspect of the present invention there is provided a method of measuring a volume of a wound, the method comprising the steps of: applying a dressing over a wound, the volume of which is to be measured, the dressing including at least a sealing drape over the wound so as to create a sealed wound cavity; creating a vacuum in said wound cavity by vacuum pump means so as to produce a predetermined vacuum in the wound cavity; measuring a volume of air extracted from said wound cavity in producing said predetermined vacuum; and, calculating a volume of said wound.

According to a second aspect of the present invention there is provided apparatus for measuring the volume of a wound, the apparatus comprising: a dressing covering and sealing the wound to form a cavity over the wound; an aspiration conduit leading from the wound cavity to a waste canister; a vacuum source; and, flow measuring sensor means.

In one embodiment of the present invention, the volume of air may be measured by signals received from flow sensor means in an apparatus control system.

Desirably, the wound volume measurement may be made at a time of dressing change and with an empty waste canister.

Desirably, the wound may be dressed in the same manner as closely as possible each time so as to minimise variables due to differences in the type and degree of packing of the wound, for example. For example, the wound may be packed with suitable filler material (if large enough and if appropriate) such as gauze, foam or any other type of filler appropriate to the wound and the sealing drape may be applied such that when the filler is compressed by the applied vacuum to the predetermined vacuum pressure then the sealing drape may be flush, for example, with the patient's sound flesh surrounding the wound. This is explanation is merely exemplary but is intended to emphasize the desirability of a consistent manner of wound dressing.

The method of the present may be applied by apparatus for the provision of TNP therapy to a patient in almost any environment. The apparatus is lightweight, may be mains or battery powered by a rechargeable battery pack contained within a device (henceforth, the term "device" is used to connote a unit which may contain all of the control, power supply, power supply recharging, electronic indicator means and means for initiating and sustaining aspiration functions to a wound and any further necessary functions of a similar nature). When outside the home, for example, the apparatus may provide for an extended period of operation on battery power and in the home, for example, the device may be connected to the mains by a charger unit whilst still being used and operated by the patient.

The overall apparatus of which the present invention is a part comprises: a dressing covering the wound and sealing at least an open end of an aspiration conduit to a cavity formed over the wound by the dressing; an aspiration tube comprising at least one lumen therethrough leading from the wound dressing to a waste material canister for collecting and holding wound exudates/waste material prior to disposal; and, a power, control and aspiration initiating and sustaining device associated with the waste canister.

The dressing covering the wound may be any type of dressing normally employed with TNP therapy and, in very general terms, may comprise, for example, a semi-permeable, flexible, self-adhesive drape material, as is known in the dressings art, to cover the wound and seal with surrounding sound tissue to create a sealed cavity or void over the wound. There may aptly be a porous barrier and support member in the cavity between the wound bed and the covering material to enable an even vacuum distribution to be achieved over the area of the wound. The porous barrier and support member being, for example, a gauze, a foam, an inflatable bag or known wound contact type material resistant to crushing under the levels of vacuum created and which permits transfer of wound exudates across the wound area to the aspiration conduit sealed to the flexible cover drape over the wound.

The aspiration conduit may be a plain flexible tube, for example, having a single lumen therethrough and made from a plastics material compatible with raw tissue, for example. However, the aspiration conduit may have a plurality of lumens therethrough to achieve specific objectives relating to the invention. A portion of the tube sited within the sealed cavity over the wound may have a structure to enable continued aspiration and evacuation of wound exudates without becoming constricted or blocked even at the higher levels of the negative pressure range envisaged.

It is envisaged that the negative pressure range for the apparatus embodying the present invention may be between about −50 mmHg and −200 mmHg (note that these pressures are relative to normal ambient atmospheric pressure thus, −200 mmHg would be about 560 mmHg in practical terms).

Aptly, the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

The aspiration conduit at its distal end remote from the dressing may be attached to the waste canister at an inlet port or connector. The device containing the means for initiating and sustaining aspiration of the wound/dressing may be situated between the dressing and waste canister, however, in a preferred embodiment of the apparatus embodying the present invention, the device may aspirate the wound/dressing via the canister thus, the waste canister may preferably be sited between the wound/dressing and device.

The aspiration conduit at the waste material canister end may preferably be bonded to the waste canister to prevent inadvertent detachment when being caught on an obstruction, for example.

The canister may be a plastics material moulding or a composite unit comprising a plurality of separate mouldings. The canister may aptly be translucent or transparent in order to visually determine the extent of filling with exudates. However, the canister and device may in some embodiments provide automatic warning of imminent canister full condition and may also provide means for cessation of aspiration when the canister reaches the full condition.

The canister may be provided with filters to prevent the exhaust of liquids and odours therefrom and also to prevent the expulsion of bacteria into the atmosphere. Such filters may comprise a plurality of filters in series. Examples of suitable filters may comprise hydrophobic filters of 0.2 μm pore size, for example, in respect of sealing the canister against bacteria expulsion and 1 μm against liquid expulsion.

Aptly, the filters may be sited at an upper portion of the waste canister in normal use, that is when the apparatus is being used or carried by a patient the filters are in an upper position and separated from the exudate liquid in the waste canister by gravity. Furthermore, such an orientation keeps the waste canister outlet or exhaust exit port remote from the exudate surface.

Aptly the waste canister may be filled with an absorbent gel such as ISOLYSEL (trade mark), for example, as an added safeguard against leakage of the canister when full and being changed and disposed of. Added advantages of a gel matrix within the exudate storing volume of the waste canister are that it prevents excessive movement, such as slopping, of the liquid, minimises bacterial growth and minimises odours.

The waste canister may also be provided with suitable means to prevent leakage thereof both when detached from the device unit and also when the aspiration conduit is detached from the wound site/dressing.

The canister may have suitable means to prevent emptying by a user (without tools or damage to the canister) such that a full or otherwise end-of-life canister may only be disposed of with waste fluid still contained.

The device and waste canister may have mutually complementary means for connecting a device unit to a waste canister whereby the aspiration means in the device unit automatically connects to an evacuation port on the waste canister such that there is a continuous aspiration path from the wound site/dressing to an exhaust port on the device.

Aptly, the exhaust port from the fluid path through the apparatus is provided with filter means to prevent offensive odours from being ejected into the atmosphere.

In general terms the device unit comprises an aspirant pump; means for monitoring pressure applied by the aspirant pump; a flowmeter to monitor fluid flow through the aspirant pump; a control system which controls the aspirant pump in response to signals from sensors such as the pressure monitoring means and the flowmeter, for example, and which control system also controls a power management system with regard to an on-board battery pack and the charging thereof and lastly a user interface system whereby various functions of the device such as pressure level set point, for example, may be adjusted (including stopping and starting of the apparatus) by a user. The device unit may contain all of the above features within a single unified casing.

When the dressing is applied to the wound a volume of air is trapped under the sealing drape in the wound cavity. When the vacuum source such as a vacuum pump, for example, is started the wound cavity is evacuated to a predetermined vacuum such as by 0.1 of an atmosphere (i.e. about 76 mmHg below atmospheric pressure). In this case 0.1 of the volume of air in the wound cavity is removed and which is measured by the flow sensor means such as a flowmeter, for example, in the control and monitoring system. The volume of air removed will be proportional to the actual volume of the wound. The volumes of other parts of the apparatus such as the aspiration conduit, the waste canister, the vacuum pump and the flow conduits in the apparatus leading to the flow sensor may be measured and/or are known and constant factors for which a correction factor may be incorporated in memory means in the control system software.

Once the desired vacuum level is achieved and is steady at that level, the various factors may be computed by the software in the control system to calculate the wound volume. It is important that the desired vacuum is at a steady state and the vacuum source such as a vacuum pump may be running slowly or intermittently to achieve such a steady state due, for example, to a leak into the wound cavity through or around the sealing drape. The software may contain appropriate data relating to the vacuum pump operating regime to calculate the steady state leak rate and to enable the control and monitoring system to apply a suitable correction factor to allow for a steady state leak rate. Thus, when the wound cavity has achieved a steady state when the vacuum level pressure is at the desired value, what the flow sensor is reading is the actual leak rate which may be used by the software to compute the correction factor applicable.

Different wound filling materials may have different compressibility from each other. Gauze, for example, is made from material fibres which themselves are virtually incompressible at the levels of vacuum under consideration in the present invention; foam materials, however, are much more compressible and thus, correction factors need to be made to allow for the type of wound filling material in use. This may be easily achieved by test cavities of known volumes used to calibrate the apparatus for different filling materials and calculate appropriate correction factors.

As noted above it is desirable that at a time of dressing change the waste canister is empty since its empty volume forms part of the correction factor incorporated into the software. However, it is not necessary that the waste canister be empty so long as its free space is known so that a suitable factor may be entered into the control and monitoring system such as by a key pad associated with the apparatus device, for example.

In the present invention the device may have means such as LED display means, for example, of displaying and storing the volume of the wound as measured at each stage such as at each dressing change time, for example, so that a record exists of the progress of wound healing. Alternatively, the device may have an output to a separate display and/or recording device where data may be held and/or displayed.

In view of the fact that the device unit contains the majority of the intrinsic equipment cost therein ideally it will also be able to survive impact, tolerate cleaning in order to be reusable by other patients.

In terms of pressure capability the aspiration means may be able to apply a maximum pressure drop of at least −200 mmHg to a wound site/dressing. The apparatus is capable of maintaining a predetermined negative pressure even under conditions where there is a small leak of air into the system and a high exudate flow.

The pressure control system may prevent the minimum pressure achieved from exceeding for example −200 mmHg so as not to cause undue patient discomfort. The pressure required may be set by the user at a number of discreet levels such as −50, −75, −100, −125, −150, −175 mmHg, for example, depending upon the needs of the wound in question and the advice of a clinician. Thus suitable pressure ranges in use may be from −25 to −80 mmHg, or −50 to −76 mmHg, or −50 to −75 mmHg as examples. The control system may also advantageously be able to maintain the set pressure within a tolerance band of +/−10 mmHg of the set point for 95% of the time the apparatus is operating given that leakage and exudation rates are within expected or normal levels.

Aptly, the control system may trigger alarm means such as a flashing light, buzzer or any other suitable alarm means when various abnormal conditions apply such as, for example: pressure outside set value by a large amount due to a gross leak of air into system; duty on the aspiration pump too high due to a relatively smaller leakage of air into the system; pressure differential between wound site and pump is too high due, for example, to a blockage or waste canister full.

The apparatus of the present invention may be provided with a carry case and suitable support means such as a shoulder strap or harness, for example. The carry case may be adapted to conform to the shape of the apparatus comprised in the joined together device and waste canister. In particular, the carry case may be provided with a bottom opening flap to permit the waste canister to be changed without complete removal of the apparatus form the carry case.

The carry case may be provided with an aperture covered by a displaceable flap to enable user access to a keypad for varying the therapy applied by the apparatus.

In order that the present invention may be more fully understood, examples will now be described by way of illustration only with reference to the accompanying drawings, of which:

Figure 1:
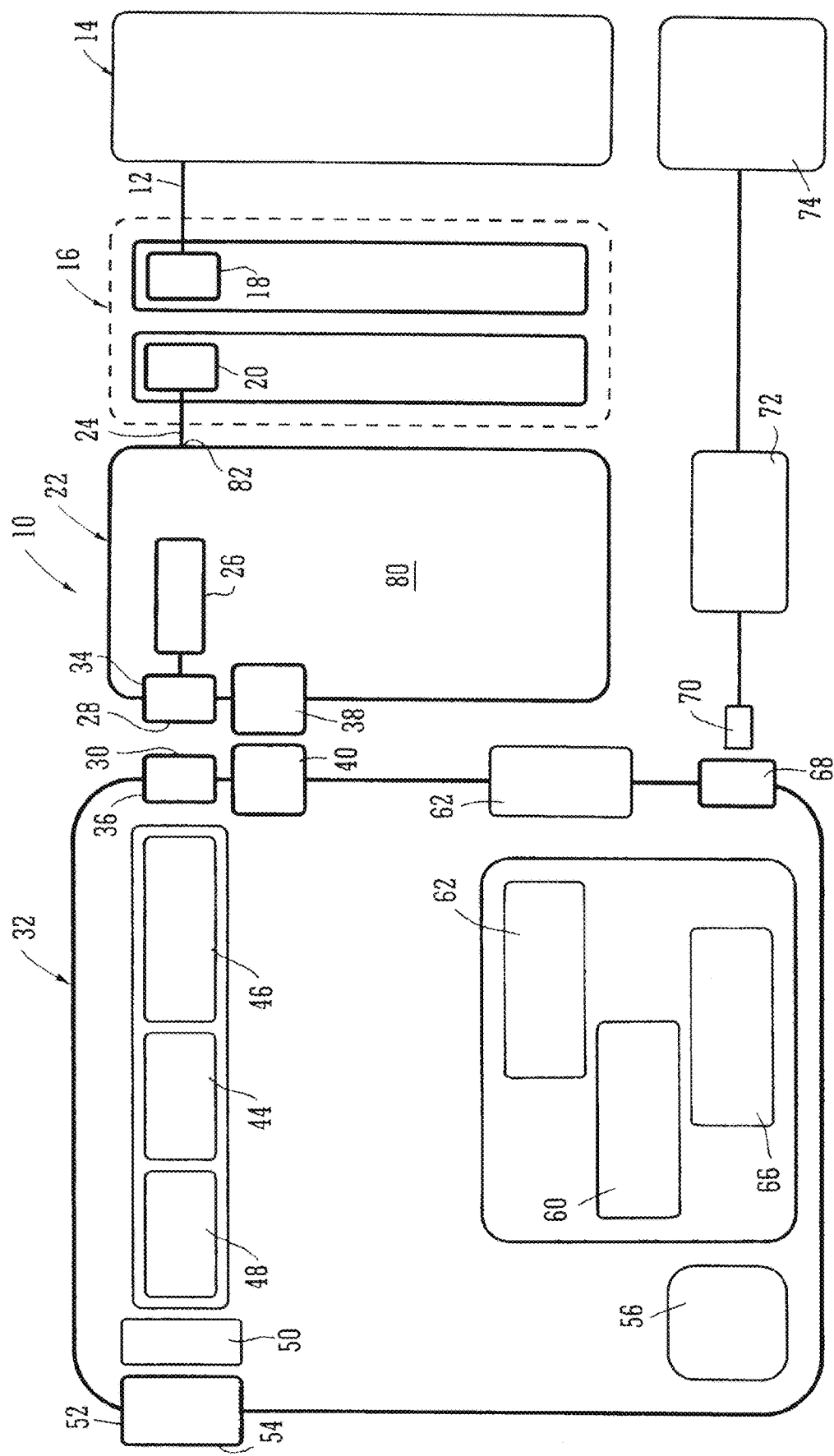
FIG. 1 shows a generalised schematic block diagram showing a general view of an apparatus and the constituent apparatus features thereof.

Referring now to FIGS. 1 to 4 of the drawings and where the same or similar features are denoted by common reference numerals.

FIG. 1 shows a generalised schematic view of an apparatus 10 of a portable topical negative pressure (TNP) system. It will be understood that embodiments of the present invention are generally applicable to use in such a TNP system. Briefly, negative pressure wound therapy assists in the closure and healing of many forms of "hard to heal" wounds by reducing tissue oedema; encouraging blood flow and granular tissue formation; removing excess exudate and may reduce bacterial load (and, therefore, infection). In addition the therapy allows for less disturbance of a wound leading to more rapid healing. The TNP system is detailed further hereinafter but in summary includes a portable body including a canister and a device with the device capable of providing an extended period of continuous therapy within at least a one year life span. The system is connected to a patient via a length of tubing with an end of the tubing operably secured to a wound dressing on the patient.

More particularly, as shown in FIG. 1, the apparatus comprises an aspiration conduit 12 operably and an outer surface thereof at one end sealingly attached to a dressing 14. The dressing 14 will not be further described here other than to say that it is formed in a known manner from well know materials to those skilled in the dressings art to create a sealed cavity over and around a wound to be treated by TNP therapy with the apparatus of the present invention. The aspiration conduit has an in-line connector 16 comprising connector portions 18, 20 intermediate its length between the dressing 14 and a waste canister 22. The aspiration conduit between the connector portion 20 and the canister 22 is denoted by a different reference numeral 24 although the fluid path through conduit portions 12 and 24 to the waste canister is continuous. The connector portions 18, 20 join conduit portions 12, 24 in a leak-free but disconnectable manner. The waste canister 22 is provided with filters 26 which prevent the escape via an exit port 28 of liquid and bacteria from the waste canister. The filters may comprise a 1 µm hydrophobic liquid filter and a 0.2 µm bacteria filter such that all liquid and bacteria is confined to an interior waste collecting volume of the waste canister 22. The exit port 28 of the waste canister 22 mates with an entry/suction port 30 of a device unit 32 by means of mutually sealing connector portions 34, 36 which engage and seal together automatically when the waste canister 22 is attached to the device unit 32, the waste canister 22 and device unit 32 being held together by catch assemblies 38, 40. The device unit 32 comprises an aspirant pump 44, an aspirant pressure monitor 46 and an aspirant flowmeter 48 operably connected together. The aspiration path takes the aspirated fluid which in the case of fluid on the exit side of exit port 28 is gaseous through a silencer system 50 and a final filter 52 having an activated charcoal matrix which ensures that no odours escape with the gas exhausted from the device 32 via an exhaust port 54. The filter 52 material also serves as noise reducing material to enhance the effect of the silencer system 50. The device 32 also contains a battery pack 56 to power the apparatus which battery pack also powers the control system 60 which controls a user interface system 62 controlled via a keypad (not shown) and the aspiration pump 44 via signals from sensors 46, 48. A power management system 66 is also provided which controls power from the battery pack 56, the recharging thereof and the power requirements of the aspirant pump 44 and other electrically operated components. An electrical connector 68 is provided to receive a power input jack 70 from a SELV power supply 72 connected to a mains supply 74 when the user of the apparatus or the apparatus itself is adjacent a convenient mains power socket.

Figure 2:
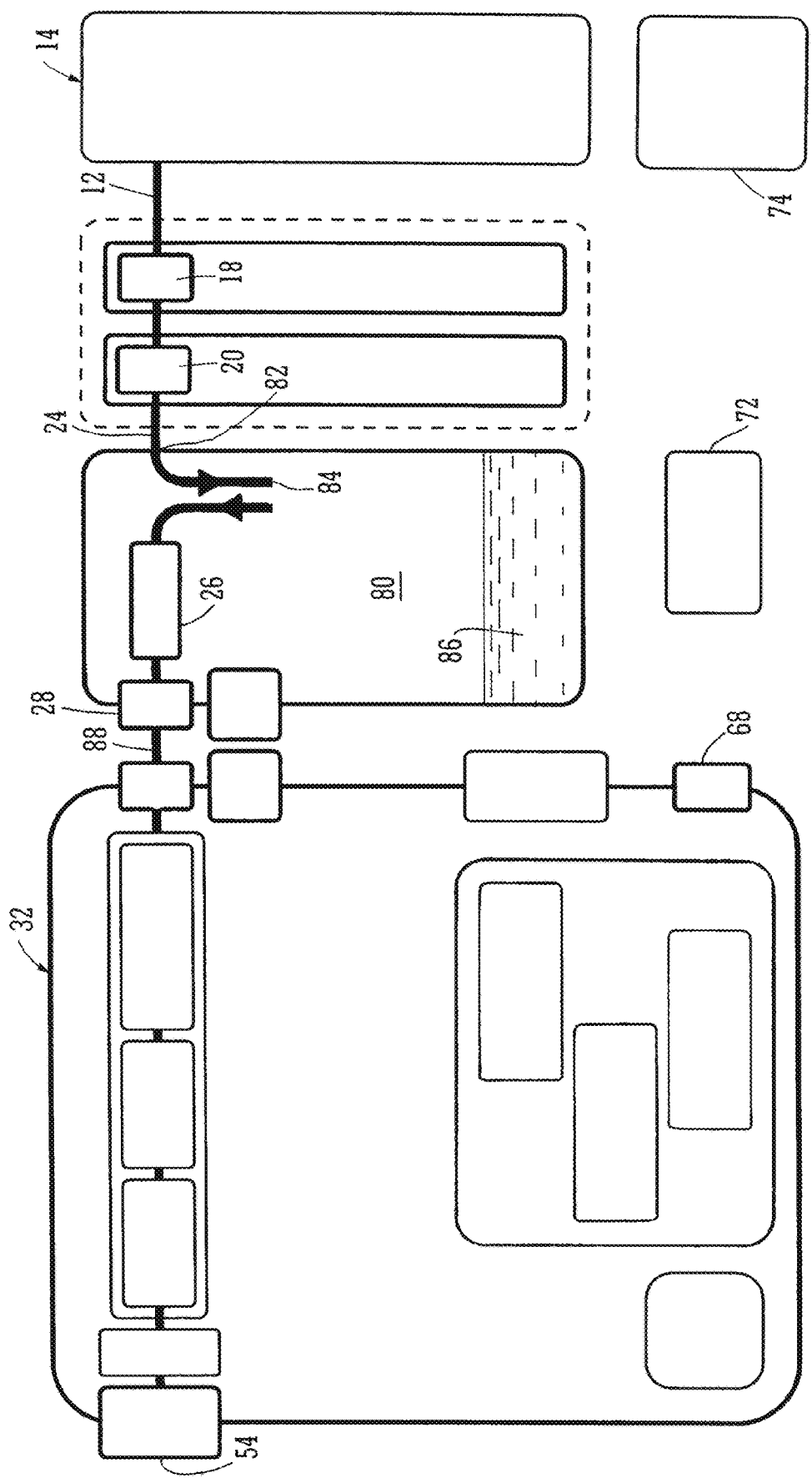
FIG. 2 shows a similar generalised schematic block diagram to FIG. 1 and showing fluid paths therein.

FIG. 2 shows a similar schematic representation to FIG. 1 but shows the fluid paths in more detail. The wound exudate is aspirated from the wound site/dressing 14 via the conduit 12, the two connector portions 18, 20 and the conduit 24 into the waste canister 22. The waste canister 22 comprises a relatively large volume 80 in the region of 500 ml into which exudate from the wound is drawn by the aspiration system at an entry port 82. The fluid 84 drawn into the canister volume 80 is a mixture of both air drawn into the dressing 14 via the semi-permeable adhesive sealing drape (not shown) and liquid 86 in the form of wound exudates. The volume 80 within the canister is also at a lowered pressure and the gaseous element 88 of the aspirated fluids is exhausted from the canister volume 80 via the filters 26 and the waste canister exhaust exit port 28 as bacteria-free gas. From the exit port 28 of the waste canister to the final exhaust port 54 the fluid is gaseous only.

Figure 3:
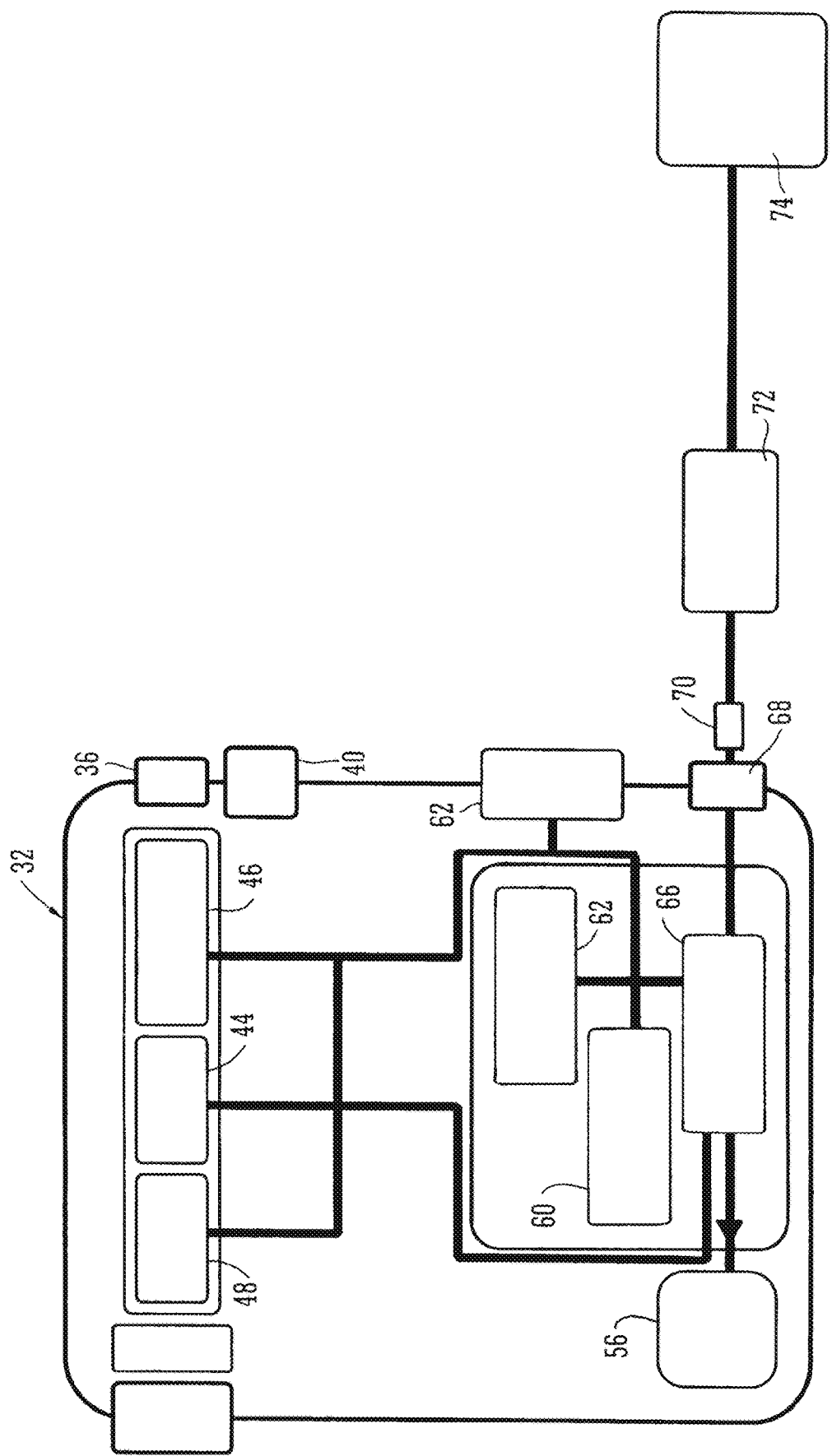
FIG. 3 shows a generalised schematic block diagram similar to FIG. 1 but of a device unit only and showing power paths for the various power consuming/producing features of the apparatus.

FIG. 3 shows a schematic diagram showing only the device portion of the apparatus and the power paths in the device of the apparatus embodying the present invention. Power is provided mainly by the battery pack 56 when the user is outside their home or workplace, for example, however, power may also be provided by an external mains 74 supplied charging unit 72 which when connected to the device 32 by the socket 68 is capable of both operating the device and recharging the battery pack 56 simultaneously. The power management system 66 is included so as to be able to control power of the TNP system. The TNP system is a rechargeable, battery powered system but is capable of being run directly from mains electricity as will be described hereinafter more fully with respect to the further figures. If disconnected from the mains the battery has enough stored charge for approximately 8 hours of use in normal conditions. It will be appreciated that batteries having other associated life times between recharge can be utilised. For example batteries providing less than 8 hours or greater than 8 hours can be used. When connected to the mains the device will run off the mains power and will simultaneously recharge the battery if depleted from portable use. The exact rate of battery recharge will depend on the load on the TNP system. For example, if the wound is very large or there is a significant leak, battery recharge will take longer than if the wound is small and well sealed.

Figure 4:
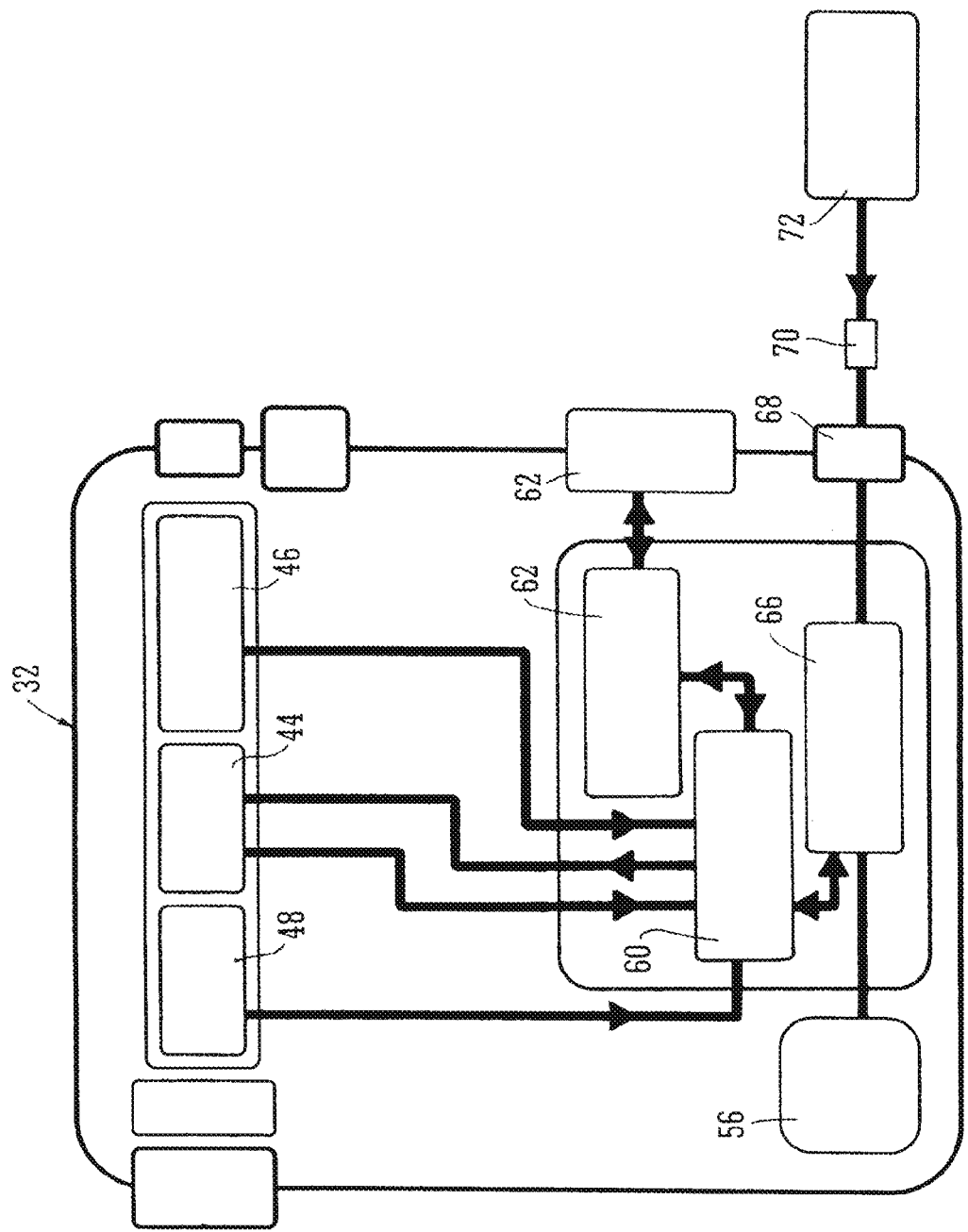
FIG. 4 shows a similar generalised schematic block diagram to FIG. 3 of the device unit and showing control system data paths for controlling the various functions and components of the apparatus.
Figure 5:
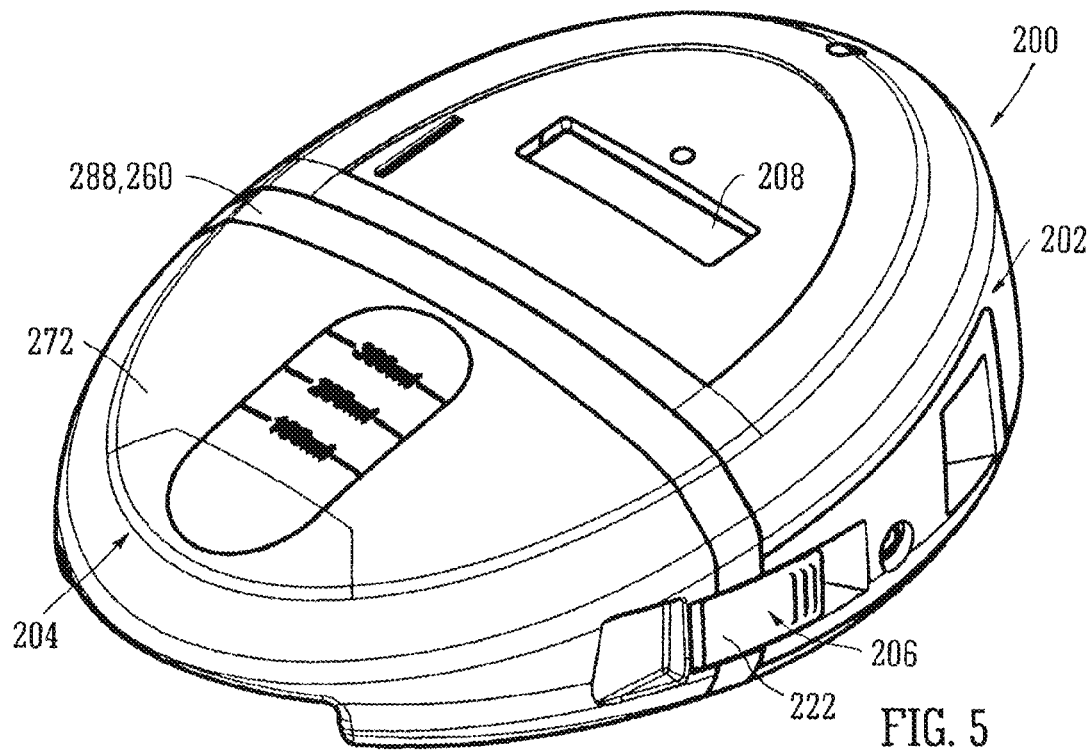
FIG. 5 shows a perspective view of an apparatus.
Figure 6:
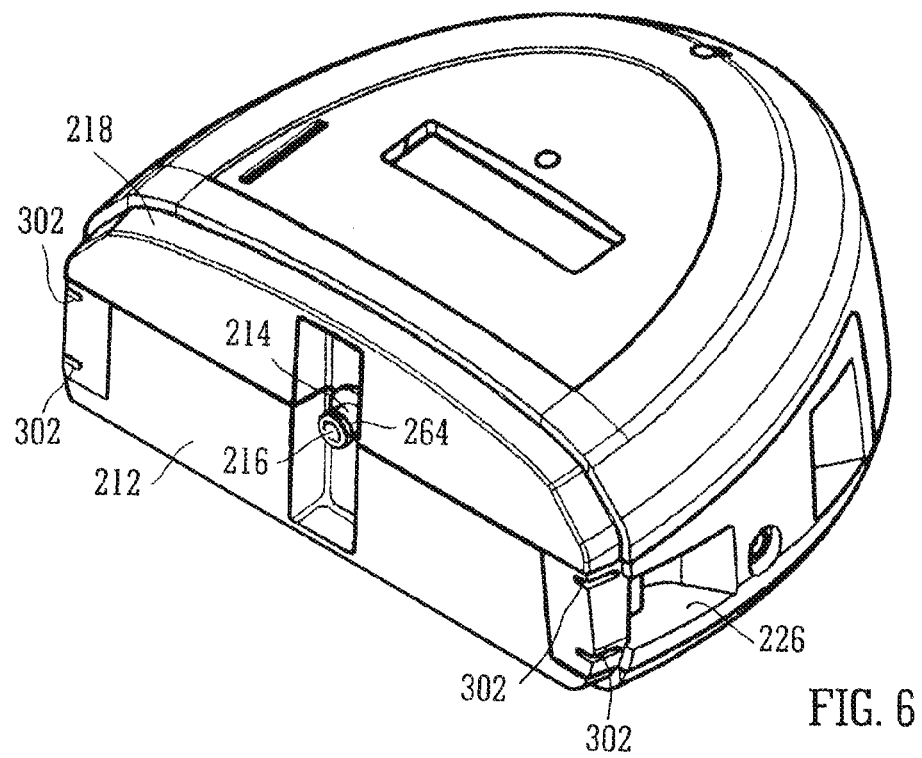
FIG. 6 shows a perspective view of an assembled device unit of the apparatus of FIG. 5.
Figure 7:
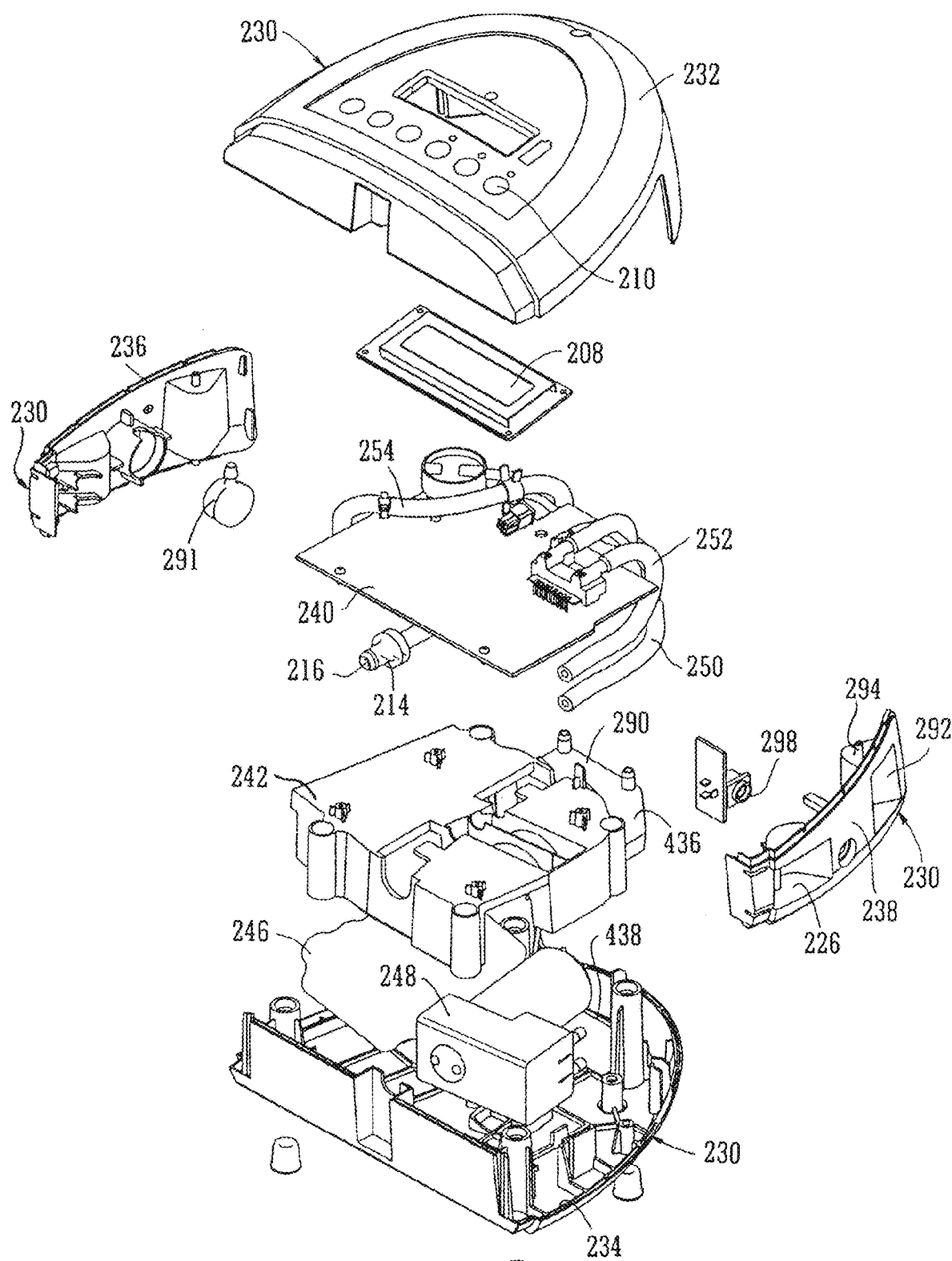
FIG. 7 shows an exploded view of the device unit of FIG. 6.

FIG. 4 shows the device 32 part of the apparatus embodying the present invention and the data paths employed in the control system for control of the aspirant pump and other features of the apparatus. A key purpose of the TNP system is to apply negative pressure wound therapy. This is accomplished via the pressure control system which includes the pump and a pump control system. The pump applies negative pressure; the pressure control system gives feedback on the pressure at the pump head to the control system; the pump control varies the pump speed based on the difference between the target pressure and the actual pressure at the pump head. In order to improve accuracy of pump speed and hence provide smoother and more accurate application of the negative pressure at a wound site, the pump is controlled by an auxiliary control system. The pump is from time to time allowed to "free-wheel" during its duty cycle by turning off the voltage applied to it. The spinning motor causes a "back electro-motive force" or BEMF to be generated. This BEMF can be monitored and can be used to provide an accurate measure of pump speed. The speed can thus be adjusted more accurately than can prior art pump systems.

According to embodiments of the present invention, actual pressure at a wound site is not measured but the difference between a measured pressure (at the pump) and the wound pressure is minimised by the use of large filters and large bore tubes wherever practical. If the pressure control measures that the pressure at the pump head is greater than a target pressure (closer to atmospheric pressure) for a period of time, the device sends an alarm and displays a message alerting the user to a potential problem such as a leak.

In addition to pressure control a separate flow control system can be provided. A flow meter may be positioned after the pump and is used to detect when a canister is full or the tube has become blocked. If the flow falls below a certain threshold, the device sounds an alarm and displays a message alerting a user to the potential blockage or full canister.

Figure 8:
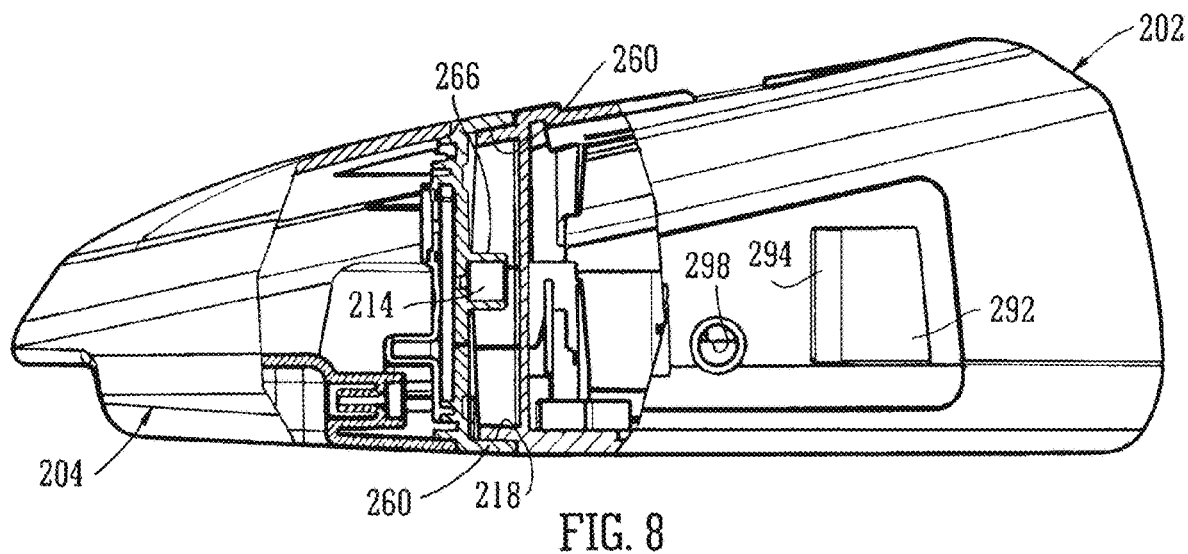
FIG. 8 shows a partially sectioned side elevation view through the interface between a waste canister and device unit of the apparatus.
Figure 9:
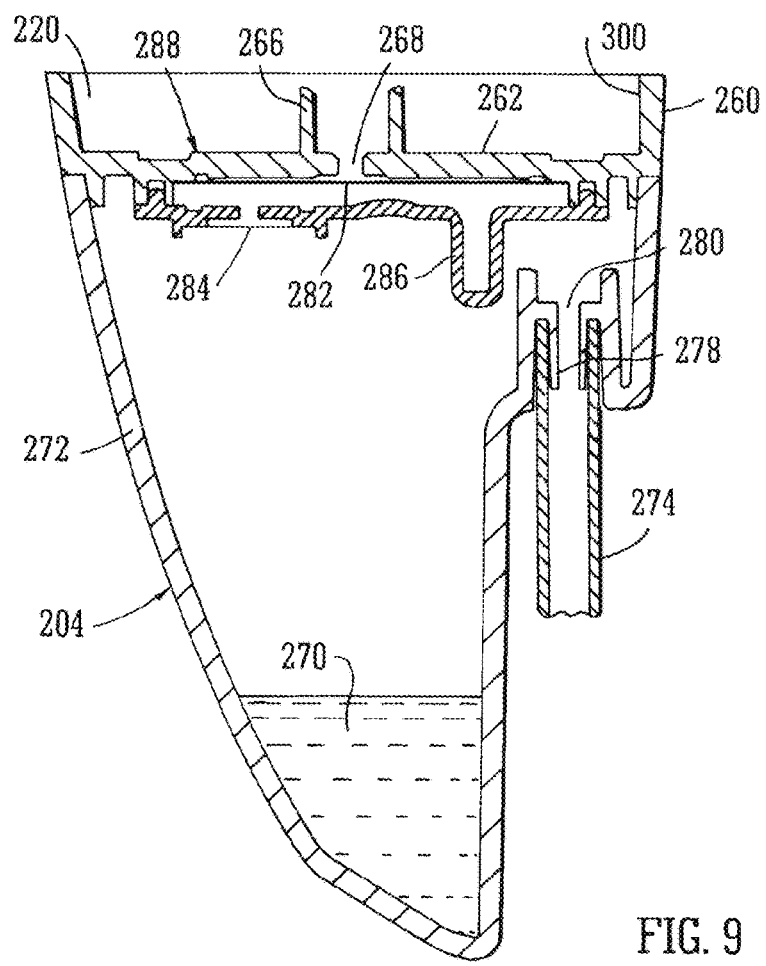
FIG. 9 shows a cross section through a waste canister of the apparatus of FIGS. 5 to 8.

Referring now to FIGS. 5 to 9 which show various views and cross sections of a preferred embodiment of apparatus 200 embodying the present invention. The preferred embodiment is of generally oval shape in plan and comprises a device unit 202 and a waste canister 204 connected together by catch arrangements 206. The device unit 202 has a liquid crystal display (LCD) 208, which gives text based feedback on the wound therapy being applied, and a membrane keypad 210, the LCD being visible through the membrane of the keypad to enable a user to adjust or set the therapy to be applied to the wound (not shown). The device has a lower, generally transverse face 212 in the centre of which is a spigot 214 which forms the suction/entry port 216 to which the aspiration means (to be described below) are connected within the device unit. The lower edge of the device unit is provided with a rebated peripheral male mating face 218 which engages with a co-operating peripheral female formation 220 on an upper edge of the waste canister 204 (see FIGS. 8 and 9). On each side of the device 202, clips 222 hinged to the canister 204 have an engaging finger (not shown) which co-operates with formations in recesses 226 in the body of the device unit. From FIG. 7 it may be seen that the casing 230 of the device unit is of largely "clamshell" construction comprising front and back mouldings 232, 234, respectively and left-hand and right-hand side inserts 236, 238. Inside the casing 230 is a central chassis 240 which is fastened to an internal moulded structural member 242 and which chassis acts as a mounting for the electrical circuitry and components and also retains the battery pack 246 and aspiration pump unit 248. Various tubing items 250, 252, 254 connect the pump unit 248 and suction/entry port 216 to a final gaseous exhaust via a filter 290. FIG. 8 shows a partially sectioned side elevation of the apparatus 200, the partial section being around the junction between the device unit 202 and the waste canister 204, a cross section of which is shown at FIG. 9. Theses views show the rebated edge 218 of the male formation on the device unit co-operating with the female portion 220 defined by an upstanding flange 260 around the top face 262 of the waste canister 204. When the waste canister is joined to the device unit, the spigot 214 which has an "O" ring seal 264 therearound sealingly engages with a cylindrical tube portion 266 formed around an exhaust/exit port 268 in the waste canister. The spigot 214 of the device is not rigidly fixed to the device casing but is allowed to "float" or move in its location features in the casing to permit the spigot 214 and seal 264 to move to form the best seal with the bore of the cylindrical tube portion 266 on connection of the waste canister to the device unit. The waste canister 204 in FIG. 9 is shown in an upright orientation much as it would be when worn by a user. Thus, any exudate 270 would be in the bottom of the internal volume of waste receptacle portion 272. An aspiration conduit 274 is permanently affixed to an entry port spigot 278 defining an entry port 280 to receive fluid aspirated from a wound (not shown) via the conduit 274. Filter members 282 comprising a 0.2 µm filter and 284 comprising a 1 µm filter are located by a filter retainer moulding 286 adjacent a top closure member or bulkhead 288 the filter members preventing any liquid or bacteria from being drawn out of the exhaust exit port 268 into the pump and aspiration path through to an exhaust and filter unit 290 which is connected to a casing outlet moulding at 291 via an exhaust tube (not shown) in casing side piece 236. The side pieces 236, 238 are provided with recesses 292 having support pins 294 therein to locate a carrying strap (not shown) for use by the patient. The side pieces 230 and canister 204 are also provided with features which prevent the canister and device from exhibiting a mutual "wobble" when connected together. Ribs (not shown) extending between the canister top closure member 288 and the inner face 300 of the upstanding flange 260 locate in grooves 302 in the device sidewalls when canister and device are connected. The casing 230 also houses all of the electrical equipment and control and power management features, the functioning of which was described briefly with respect to FIGS. 3 and 4 hereinabove. The side piece 238 is provided with a socket member 298 to receive a charging jack from an external mains powered battery charger (both not shown).

Figure 10:
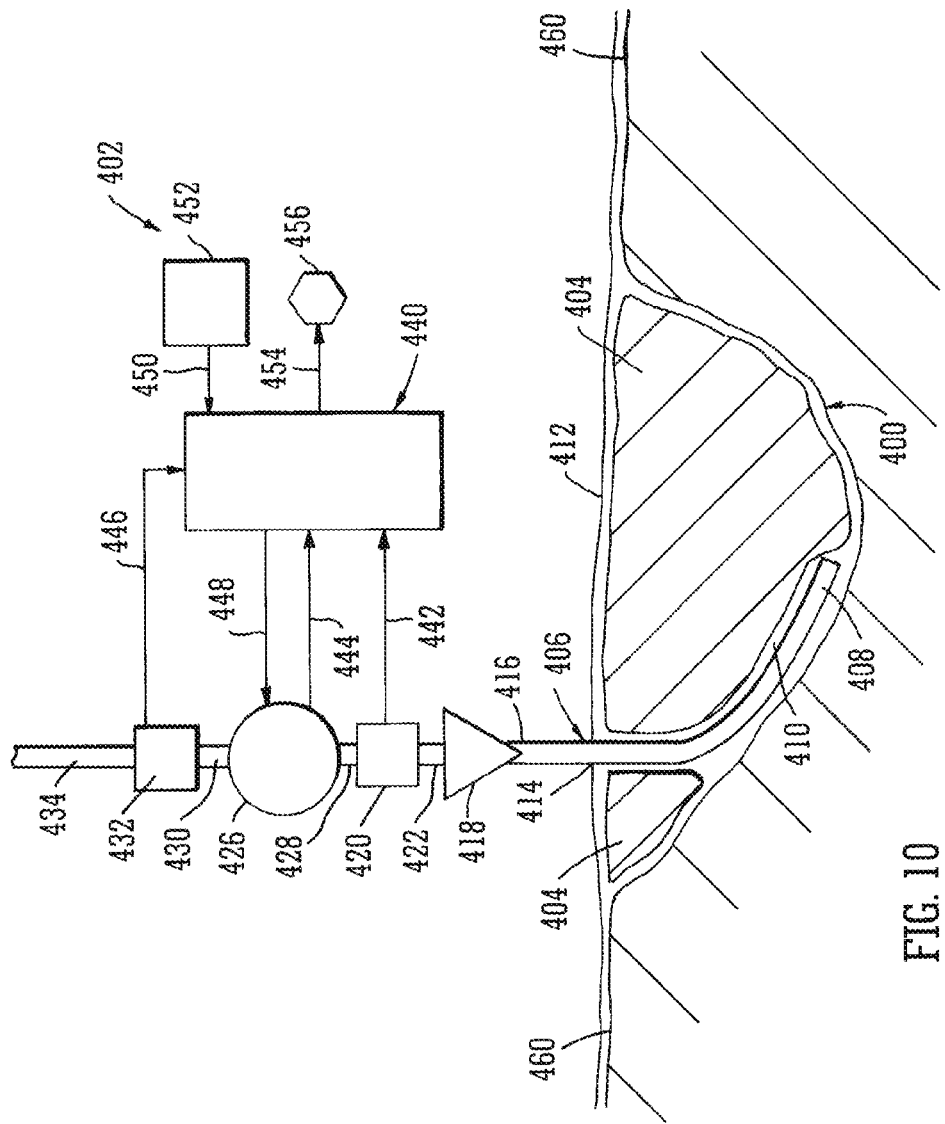
FIG. 10 shows a schematic cross section of a wound, the volume of which is to be measured, the wound having apparatus for the application of TNP therapy thereto.

FIG. 10 shows a schematic cross section of a wound 400 and apparatus 402 connected thereto to apply TNP therapy to the wound and to measure its volume. The apparatus comprises wound filling material 404; an aspirant conduit 406 having one end 408 sealed within the wound cavity 410 by an overlying sealing drape 412 at point 414 and a distal end 416 of the conduit 406 attached to a waste canister 418 for the collection of exudate from the wound. The waste canister is operably connected to a pressure sensor 420 by a conduit portion 422 and to the inlet side of a vacuum pump 426 by a conduit portion 428. The vacuum pump output side is connected by a conduit portion 430 to a flow sensor 432 and exhaust is taken away via a conduit 434. A control and monitoring system is provided at 440 and receives signals 442 from the pressure sensor 420; receives signals 444 from the vacuum pump; and, receives signals 446 from the flow sensor 432. The control system 440 sends control signals 448 to the vacuum pump 426 in order for it to maintain a steady state pressure as set by instructions 450 entered by a clinician/user on a data entry keypad 452. The control system 440 outputs data 454 to a display 456 such as an LCD display, for example, as required by the clinician/user in response to instructions 450 but includes data relating to the volume of the wound 400. The sealing drape 412 is sealed to the patient's sound flesh at 460 surrounding the wound 400 generally by a layer of pressure sensitive adhesive (not shown) on the flesh contacting side of the drape 412.

In operation a clinician/user enters a required pressure, consistent with calibration procedures previously employed, to be achieved in the wound cavity 410 on the keypad 452. The vacuum pump 426 is initiated and pumps the wound cavity 410 down to the required pressure and continues to operate as appropriate to maintain the required pressure at a steady state. The apparatus 402 has been calibrated in that the volumes of the conduit 406; empty waste canister 418; conduits 422, 428, 430; and vacuum pump 426 are known and a correction factor has been entered in the memory of the control system 440.

Figure 11:
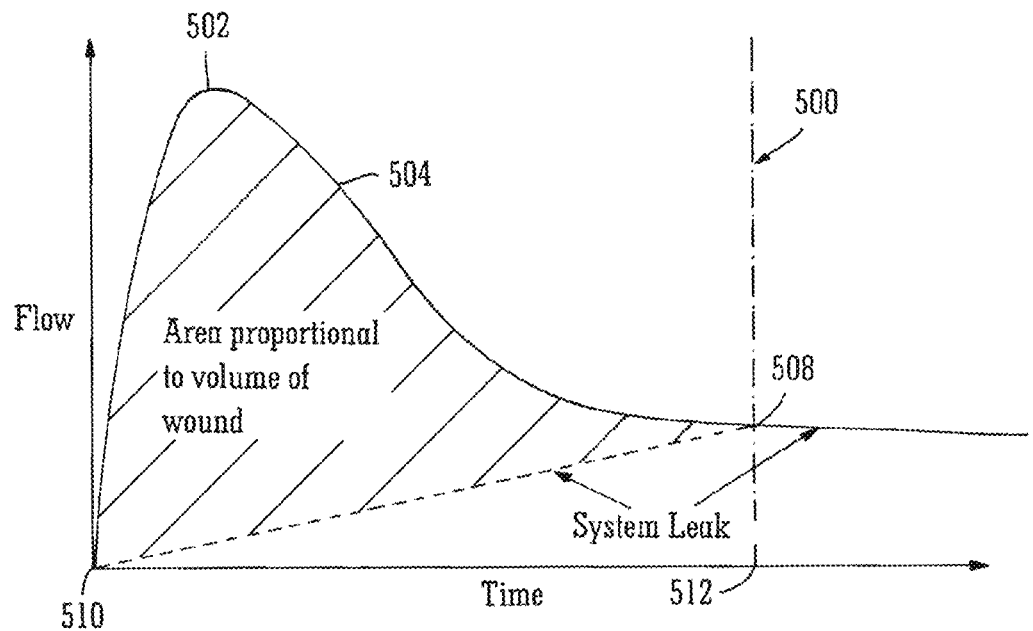
FIG. 11 shows a graph of flow vs time of an example of wound volume measurement.

FIG. 11 shows a graph of fluid flow, in this case air against time to achieve steady state conditions. FIG. 11 indicates time taken to reach a steady state pressure as set in the control system at start up and which time to reach a steady state pressure is indicated by the line 500. Initially the rate of air flow rises rapidly to a maximum at 502 after which the flow rate falls off as the set pressure is approached and the steady state is achieved at line 502. Part of the flow rate under the curve 504 may probably be due to an inward leak of air, most probably into the wound cavity 410 (the joints between the component parts of the apparatus from the conduit 406 in the direction of fluid flow should all be sound and leak-free) between the sealing drape 412 and the patient's sound flesh 460. The point 508 indicates the steady state flow rate to maintain the desired set pressure and the area of the triangle 510, 508, 512 indicates the portion or volume of air aspirated from the wound cavity attributable to the leak and may be deducted from the total area under the curve 504 up to the line 500. Thus, the control and monitoring system 440 computes the volume of the wound from the area under the curve 504 bounded by the line 508-510 and will be displayed on the display 456 and/or in suitable recording apparatus (not shown).

Figure 12:
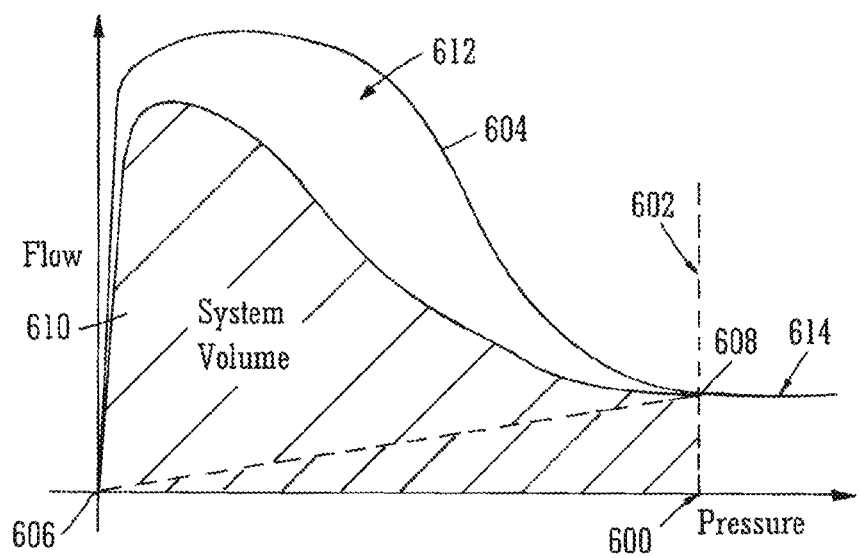
FIG. 12 which shows a graph of flow against pressure in the wound cavity.

A similar graph to that of FIG. 11 and shown in FIG. 12 may be drawn but showing flow against pressure in the wound cavity 410. Steady state is reached when the set pressure has been achieved. In the graph of FIG. 12 the set pressure 600 and steady state coincide at the line 602 and the total area under the curve 604 is comprised of: a factor relating to leak rate as before and is the triangular area 600, 606, 608; a factor relating to system volume indicated by the vertically hatched area 610 and the wound volume indicated by the area 612. When the system is at a steady state indicated by the line 614 the flow through the flow sensor relates only to the leakage into the system.

The volume of the wound may be computed from the expression:

$$V_{wound} = \text{Area under curve} \frac{\times (760 - \text{Set pressure in mmHg})}{760}$$

If the dressing drape 412 is completely leak-free then the steady state flow rate when the set required pressure is reached will be zero and the point 508 will lie on the time axis.

The flow meter 432 is shown as situated after the vacuum pump 426 but may in other embodiments of apparatus according to the present invention lie between the waste canister 418 and the vacuum pump 426. Suitable correction factors relating to the exact arrangement of apparatus used will need to be determined.

The method of the present invention may be carried out by the apparatus described and discussed with reference to FIGS. 1 to 9 above which also constitutes apparatus according to the present invention.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. A negative pressure wound therapy device comprising:
a negative pressure source configured to be connected to a wound via a fluid flow path and to provide negative pressure to the wound; and
a controller programmed to operate the negative pressure source, the controller further programmed to:
monitor a cumulative fluid flow rate in the fluid flow path, the cumulative fluid flow rate comprising a first fluid flow rate due to operation of the negative pressure source and a second fluid flow rate due to a leak in the fluid flow path,
determine the second fluid flow rate due to the leak in the fluid flow path,
determine a volume of the wound based on the cumulative fluid flow rate and the second fluid flow rate due to the leak in the fluid flow path, and
provide an indication of the volume of the wound.

2. The device of claim 1, wherein the controller is programmed to:
provide an indication of the second fluid flow rate due to the leak.

3. The device of claim 2, wherein the controller is programmed to:
determine the second fluid flow rate responsive to the negative pressure source operating in a steady state.

4. The device of claim 3, wherein in the steady state, the second fluid flow rate is equivalent to the cumulative fluid flow rate.

5. The device of claim 3, further comprising a pressure sensor configured to measure pressure in the fluid flow path, wherein the steady state is determined based on the measured pressure.

6. The device of claim 5, wherein the pressure sensor is configured to be positioned in the fluid flow path between the negative pressure source and a wound dressing covering the wound.

7. The device of claim 1, further comprising a display configured to display information relating to the cumulative fluid flow rate.

8. The device of claim 1, further comprising a flow sensor configured to monitor the cumulative fluid flow rate.

9. The device of claim 8, wherein the flow sensor comprises a flow meter.

10. The device of claim 1, wherein the controller is programmed to:
 determine and apply a correction factor to the cumulative fluid flow rate to determine the first fluid flow rate due to the operation of the negative pressure source.

11. A kit comprising the device of claim 1 and a wound dressing configured to cover the wound.

12. A non-transitory computer readable medium storing instructions that, when executed by a controller of a negative pressure wound therapy device, cause the controller to:
 via a fluid flow path, operate a negative pressure source to provide negative pressure to a wound covered by a wound dressing;
 measure a cumulative fluid flow rate, wherein the cumulative fluid flow rate comprises a first fluid flow rate due to operation of the negative pressure source and a second fluid flow rate due to a leak in the fluid flow path;
 determine the second fluid flow rate due to the leak in the fluid flow path;
 determine a volume of the wound based on the cumulative fluid flow rate and the second fluid flow rate due to the leak in the fluid flow path; and
 provide an indication of the volume of the wound.

13. The medium of claim 12, wherein the instructions further cause the controller to:
 determine and apply a correction factor to the cumulative fluid flow rate to determine the first fluid flow rate due to operation of the negative pressure source.

14. The medium of claim 13, wherein the instructions further cause the controller to provide an indication of the cumulative fluid flow rate.

15. The medium of claim 14, wherein the indication comprises a visual indication.

16. The medium of claim 12, wherein the instructions further cause the controller to determine the second fluid flow rate responsive to the negative pressure source operating in a steady state.

17. The medium of claim 16, wherein in the steady state, the second fluid flow rate is equivalent to the cumulative fluid flow rate.

18. The medium of claim 16, wherein the steady state is determined based on monitoring pressure in the fluid flow path.

* * * * *